United States Patent
Kalgutkar et al.

(10) Patent No.: US 7,030,169 B2
(45) Date of Patent: *Apr. 18, 2006

(54) ARYLSULFINATE SALTS IN INITIATOR SYSTEMS FOR POLYMERIC REACTIONS

(75) Inventors: Rajdeep S. Kalgutkar, St. Paul, MN (US); Michael C. Palazzotto, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 108 days.

This patent is subject to a terminal disclaimer.

(21) Appl. No.: 10/672,762

(22) Filed: Sep. 26, 2003

(65) Prior Publication Data

US 2005/0070622 A1    Mar. 31, 2005

(51) Int. Cl.
  *C08F 4/00*  (2006.01)
  *C08G 1/56*  (2006.01)
  *C08G 1/73*  (2006.01)

(52) U.S. Cl. ............... 522/31; 522/59; 522/50; 526/193; 526/198

(58) Field of Classification Search ............ 522/31, 522/50, 59; 526/193, 198
  See application file for complete search history.

(56) References Cited

U.S. PATENT DOCUMENTS

| | | | |
|---|---|---|---|
| 3,556,794 A | 1/1971 | Margerum | |
| 3,573,922 A | 4/1971 | Rust | |
| 3,607,272 A | 9/1971 | Rust | |
| 3,623,875 A | 11/1971 | Desjarlais | |
| 3,627,656 A | 12/1971 | Miller et al. | |
| 3,642,487 A | 2/1972 | Rust | |
| 3,708,296 A | 1/1973 | Schlesinger | |
| 3,729,313 A | 4/1973 | Smith | |
| 3,741,769 A | 6/1973 | Smith | |
| 3,788,858 A | 1/1974 | Margerum | |
| 3,808,006 A | 4/1974 | Smith | |
| 4,069,054 A | 1/1978 | Smith | |
| 4,069,055 A | 1/1978 | Crivello | |
| 4,182,035 A | 1/1980 | Yamauchi et al. | |
| 4,216,288 A | 8/1980 | Crivello | |
| 4,250,053 A | 2/1981 | Smith | |
| 4,250,311 A | 2/1981 | Crivello | |
| 4,257,915 A | 3/1981 | Eaton | |
| 4,259,075 A | 3/1981 | Yamauchi et al. | |
| 4,356,296 A | 10/1982 | Griffith et al. | |
| 4,366,228 A | 12/1982 | Specht et al. | |
| 4,394,403 A | 7/1983 | Smith | |
| 4,455,147 A | 6/1984 | Lewis et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,642,126 A | 2/1987 | Zador et al. | |
| 4,650,913 A | 3/1987 | Feiring | |
| 4,652,274 A | 3/1987 | Boettcher et al. | |
| 4,665,217 A | 5/1987 | Reiners et al. | |
| 4,695,251 A | 9/1987 | Randklev | |
| 4,752,338 A | 6/1988 | Reiners et al. | |
| 4,755,620 A * | 7/1988 | Iwamoto et al. | 560/224 |
| 4,859,572 A * | 8/1989 | Farid et al. | 430/281.1 |
| 4,871,786 A | 10/1989 | Aasen et al. | |
| 4,872,936 A | 10/1989 | Engelbrecht | |
| 4,908,227 A | 3/1990 | Dougherty et al. | |
| 4,959,297 A | 9/1990 | Palazzotto | |
| 4,966,934 A * | 10/1990 | Huang et al. | 524/315 |
| 4,971,892 A * | 11/1990 | Ali et al. | 430/281.1 |
| 4,983,644 A * | 1/1991 | Mukai et al. | 522/14 |
| 5,076,844 A | 12/1991 | Fock et al. | |
| 5,084,586 A | 1/1992 | Farooq | |
| 5,089,374 A | 2/1992 | Saeva | |
| 5,105,006 A * | 4/1992 | Parker | 562/30 |
| 5,124,417 A | 6/1992 | Farooq | |
| 5,130,347 A | 7/1992 | Mitra | |
| 5,154,762 A | 10/1992 | Mitra et al. | |
| 5,256,447 A | 10/1993 | Oxman et al. | |
| 5,304,585 A * | 4/1994 | Bunker | 523/116 |
| 5,486,544 A * | 1/1996 | Kawashima et al. | 522/17 |
| 5,501,727 A | 3/1996 | Wang et al. | |
| 5,530,038 A | 6/1996 | Yamamoto et al. | |
| 5,545,676 A | 8/1996 | Palazzotto et al. | |
| 5,607,663 A | 3/1997 | Rozzi et al. | |
| 5,662,887 A | 9/1997 | Rozzi et al. | |
| 5,866,630 A | 2/1999 | Mitra et al. | |
| 5,876,208 A | 3/1999 | Mitra et al. | |

(Continued)

FOREIGN PATENT DOCUMENTS

DE    2 215 474    10/1973

(Continued)

OTHER PUBLICATIONS

Connors, K. A., "*Chemical Kinetics, The Study of Reaction Rates in Solution*", VCH, 1990, Chapter 2.

(Continued)

*Primary Examiner*—Susan Berman
(74) *Attorney, Agent, or Firm*—Jean A. Lown

(57) ABSTRACT

Compositions are provided that that can be used as an initiator system for free radical polymerization reactions. More specifically, the initiator systems include an electron acceptor and an electron donor. The electron donors are arylsulfinate salts having a cation that contains at least one carbon atom and either a positively charged nitrogen atom or a positively charged phosphorus atom. Methods of polymerization are also provided that can be used to prepare polymeric material with the initiator systems. The initiator systems can be thermal initiator systems, photoinitiator systems, or combinations thereof.

23 Claims, No Drawings

U.S. PATENT DOCUMENTS

| | | | |
|---|---|---|---|
| 5,888,491 | A | 3/1999 | Mitra et al. |
| 5,998,495 | A | 12/1999 | Oxman et al. |
| 6,017,660 | A | 1/2000 | Palazzotto et al. |
| 6,030,606 | A | 2/2000 | Holmes |
| 6,187,833 | B1 | 2/2001 | Oxman et al. |
| 6,204,302 | B1 | 3/2001 | Rawls et al. |
| 6,312,668 | B1 | 11/2001 | Mitra et al. |
| 6,331,080 | B1 | 12/2001 | Cole et al. |
| 6,387,981 | B1 | 5/2002 | Zhang et al. |
| 6,444,725 | B1 | 9/2002 | Trom et al. |
| 6,566,413 | B1 | 5/2003 | Weinmann et al. |
| 6,624,236 | B1 | 9/2003 | Bissinger et al. |
| 6,759,177 | B1 | 7/2004 | Shimada et al. |
| 2003/0054288 | A1 | 3/2003 | Shimada et al. |
| 2003/0166816 | A1 | 9/2003 | Bissinger et al. |

FOREIGN PATENT DOCUMENTS

| | | |
|---|---|---|
| EP | 0 201 031 | 11/1986 |
| EP | 0 201 778 | 11/1986 |
| EP | 0 237 233 | 9/1987 |
| EP | 0 373 384 | 6/1990 |
| EP | 0375160 | 6/1990 |
| EP | 0 661 034 | 7/1995 |
| EP | 0 712 622 | 5/1996 |
| EP | 1 051 961 | 11/2000 |
| EP | 1 269 967 | 1/2003 |
| JP | 9-34110 | 2/1997 |
| JP | 2002-341519 | 11/2002 |
| WO | WO 00/38619 | 7/2000 |
| WO | WO 00/42092 | 7/2000 |
| WO | WO 01/07444 | 2/2001 |
| WO | WO 01/30306 | 5/2001 |
| WO | WO 01/30307 | 5/2001 |
| WO | WO 01/92271 | 12/2001 |
| WO | WO 02/092021 | 11/2002 |

OTHER PUBLICATIONS

Rodrigues et al., "*Cationic Photopolymerization Of Tetrahydrofuran: A Mechanistic Study On The Use Of A Sulfonium Salt-Phenothiazine Initiation System*", Journal of Polymer Science: Part A: Polymer Chemistry, vol. 39, pp. 46-55, 2001.

Gomurashvili et al., "*Phenothiazine Photosensitizers For Onium Salt Photoinitiated Cationic Polymerization*", Journal of Polymer Science: Part A: Polymer Chemistry, vol. 39, pp. 1187-1197, 2001.

Crivello et al., "*Dye-Sensitized Photoinitiated Cationic Polymerization. The System: Perylene-Triarylsulfonium Salts*", General Electric Corporate Research and Development, Schenectady, NY, pp. 1059-1065.

"*Pigments-Inorganic*" and "*Pigments-Organic*", Kirk-Othmer Encyclopedia of Chemical Technology, Third ed., vol. 17, pp. 788-871, John Wiley & Sons, NY, 1982.

Pearson, "*Photoconductive Polymers*", Pure and Appl. Chem., 49, pp. 463-477, 1977.

Beringer et al., "*Diaryliodonium Salts. IX. The Synthesis of Substituted Diphenyliodonium Salts*", Am. Chem. Soc., 81, 342-351 (1959).

Dorman et al., "*Carbon-13 Nuclear Magnetic Resonance Spectroscopy. Quantitative Correlations of the Carbon Chemical Shifts of Acyclic Alkenes*", J. Org. Chem., 36, 2757-2766 (1971).

Sims et al., "*Studies on the Mechanism by Which Cyanine Dyes Measure Membrane Potential in Red Blood Cells and Phosphatidylcholine Vesicles*", Biochemistry, vol. 13, No. 16, 3315-3330 (1974).

Safran et al., "*Phase Diagrams for Microemulsions*", Phys. Rev.Lett., vol. 50, No. 24, pp. 1930-1933 (1983).

Buonocore et al., "*A Report on A Resin Composition Capable Of Bonding To Human Dentin Surfaces*", J.Dent. Res., vol. 35, No. 6, pp. 846-851 (1956).

Leung et al., "*Microemulsions: Formation, Structure, Properties, and Novel Applications*", Surfactants in Chemical/Process Engineering, Marcel Dekker, Inc. NY, vol. 28, Chapter 9, pp. 315-367 (1988).

Ostrovsky et al., "*Mechanism of Microemulsion Formation In Systems With Low Interfacial Tension: Occurrence, Properties, and Behavior of Microemulsions*", J.Colloid. Interface.Sci., vol. 102, No. 1, pp. 206-226 (1984).

\* cited by examiner

US 7,030,169 B2

ARYLSULFINATE SALTS IN INITIATOR SYSTEMS FOR POLYMERIC REACTIONS

TECHNICAL FIELD

Arylsulfinate salts are provided that can be used as electron donors in initiator systems for free radical polymerization reactions.

BACKGROUND

Free radical polymerization reactions typically have an initiator system. The initiator systems can be based on various chemical approaches. For example, free radical polymerization reactions can be initiated using a three-component photoinitiator system that includes an electron acceptor, an electron donor, and a sensitizing compound. Alternatively, an electron donor in combination with a sensitizing compound can be used as a photoinitiator system. Free radical polymerization reactions also can be initiated using a two-component thermal initiator system that includes an electron acceptor and an electron donor.

In thermally initiated free radical polymerization reactions, an electron donor usually reacts directly with an electron acceptor to reduce the electron acceptor. The reduced electron acceptor can be a radical that can function as an initiating free radical for the polymerization reaction. The reaction between the electron donor and acceptor can occur at room temperature or at elevated temperatures. The electron acceptor and the electron donor are often kept in separate containers (i.e., not mixed together) until polymerization is desired.

In contrast to thermally initiated systems, the components of a photoinitiator system usually can be mixed together prior to use. In a three-component photoinitiator system that includes an electron donor, electron acceptor and a sensitizing compound, there is typically no direct reaction between the electron donor and the electron acceptor. Rather, the sensitizing compound usually absorbs actinic radiation resulting in the formation of an excited sensitizing compound. The electron donor can donate an electron to the excited sensitizing compound. That is, the sensitizing compound is reduced and the electron donor is oxidized. The reduced sensitizing compound is a radical anion that can donate an electron to an electron acceptor to yield an initiating free radical for the polymerization reaction. The initiating free radical is the reduced electron acceptor. In some instances of a three-component photoinitiator system, the oxidized electron donor is a radical species that also can function as an initiating free radical.

Other photoinitiator systems include a sensitizing compound and an electron donor but no electron acceptor. The sensitizing compound can absorb actinic radiation to form an exited sensitizing compound. The electron donor can donate an electron to the excited sensitizing compound resulting in the oxidation of the electron donor. The oxidized electron donor is a radical species that functions as an initiating free radical for polymerization reactions.

SUMMARY

Compositions are provided that include an electron donor and an electron acceptor. More specifically, the electron donor is an arylsulfinate salt. Methods of polymerization are provided that can be used to prepare polymeric material using a free radical polymerization reaction. The polymerization reaction is initiated with a photoinitiator system, thermal initiator system, or combinations thereof.

One aspect of the invention provides a composition that includes an electron donor and an electron acceptor. The electron donor has an oxidation potential in N,N-dimethylformamide of 0.0 to +0.4 volts versus a silver/silver nitrate reference electrode and includes an arylsulfinate salt having an anion of Formula I

$$Ar^1\text{---}SO_2^- \qquad \text{I}$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The electron acceptor has a reduction potential in N,N-dimethylformamide of +0.4 to −1.0 volts versus a silver/silver nitrate reference electrode. The composition can further include a sensitizing compound, ethylenically unsaturated monomers, hydroxy-containing material, or combinations thereof.

A second aspect of the invention provides a photopolymerization method that includes irradiating a photopolymerizable composition with actinic radiation until the photopolymerizable composition gels or hardens. The photopolymerizable composition includes an ethylenically unsaturated monomer, a sensitizing compound, an electron donor, and an electron acceptor. The sensitizing compound is capable of absorbing a wavelength of actinic radiation in the range of 250 to 1000 nanometers. The electron acceptor has a reduction potential in N,N-dimethylformamide of +0.4 to −1.0 volts versus a silver/silver nitrate reference electrode and forms a colorless solution when dissolved in an alcohol or an ethylenically unsaturated monomer. The electron donor has an oxidation potential in N,N-dimethylformamide of 0.0 to +0.4 volts versus a silver/silver nitrate reference electrode and includes an arylsulfinate salt. The arylsulfinate salt has an anion of Formula I

$$Ar^1\text{---}SO_2^- \qquad \text{I}$$

and a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

A third aspect of the invention provides a method of polymerization that includes forming a polymerizable composition and reacting the polymerizable composition. The polymerizable composition includes an ethylenically unsaturated monomer, an electron donor having an oxidation potential in N,N-dimethylformamide of 0.0 to +0.4 volts versus a silver/silver nitrate reference electrode, and an electron acceptor having a reduction potential in N,N-dimethylformamide of +0.4 to −1.0 volts versus a silver/silver nitrate reference electrode. The electron donor is an arylsulfinate salt having an anion of Formula I

$$Ar^1\text{---}SO_2^- \qquad \text{I}$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

The above summary is not intended to describe each disclosed embodiment or every implementation of the present invention. The detailed description section that follow more particularly exemplify these embodiments.

DETAILED DESCRIPTION

Compositions are provided that include an electron donor and an electron acceptor. More specifically, the electron donor is an arylsulfinate salt. Methods of polymerization are also provided that can be used to prepare polymeric material from a polymerizable composition. The polymerizable composition includes an initiator system with an arylsulfinate salt as the electron donor. The initiator system can be a thermal initiator system, photoinitiator system, or combinations thereof.

Definitions

As used herein, the terms "a", "an", and "the" are used interchangeably with "at least one" to mean one or more of the elements being described.

As used herein, the term "actinic radiation" refers to electromagnetic radiation capable of producing photochemical activity.

As used herein, the term "acyl" refers to a monovalent group of formula —(CO)$R^a$ where $R^a$ is an alkyl or aryl group.

As used herein, the term "alkenyl" refers to a monovalent radical of an alkene (i.e., an alkene is an aliphatic compound having at least one carbon-carbon double bond).

As used herein, the term "alkoxy" refers to a group of formula —OR where R is an alkyl group. Examples include methoxy, ethoxy, propoxy, butoxy, and the like.

As used herein, the term "alkoxycarbonyl" refers to a monovalent group of formula —(CO)OR where R is an alkyl group. An example is ethoxycarbonyl.

As used herein, the term "alkoxysulfonyl" refers to a monovalent group having the formula —SO$_3$R where R is an alkyl group.

As used herein, the term "alkyl" refers to a monovalent radical of an alkane. The alkyl can be linear, branched, cyclic, or combinations thereof and typically contains 1 to 30 carbon atoms. In some embodiments, the alkyl group contains 1 to 20, 1 to 14, 1 to 10, 4 to 10, 4 to 8, 1 to 6, or 1 to 4 carbon atoms. Examples of alkyl groups include, but are not limited to methyl, ethyl, n-propyl, isopropyl, n-butyl, tert-butyl, isobutyl, n-pentyl, n-hexyl, cyclohexyl, n-octyl, n-heptyl, and ethylhexyl.

As used herein, the term "alkylsulfonyl" refers to a monovalent group of formula —SO$_2$R where R is an alkyl group.

As used herein, the term "alkynyl" refers to a monovalent radical of an alkyne (i.e., an alkyne is an aliphatic compound having at least one carbon-carbon triple bond).

As used herein, the term "amino" refers to a monovalent group of formula —NR$^b{}_2$ where each $R^b$ is independently a hydrogen, alkyl, or aryl group. In a primary amino group, each $R^b$ group is hydrogen. In a secondary amino group, one of the $R^b$ groups is hydrogen and the other $R^b$ group is either an alkyl or aryl. In a tertiary amino group, both of the $R^b$ groups are an alkyl or aryl.

As used herein, the term "aminocarbonyl" refers to a monovalent group of formula —(CO)NR$^b{}_2$ where each $R^b$ is independently a hydrogen, alkyl, or aryl.

As used herein, the term "aromatic" refers to both carbocyclic aromatic compounds or groups and heteroaromatic compounds or groups. A carbocyclic aromatic compound is a compound that contains only carbon atoms in an aromatic ring structure. A heteroaromatic compound is a compound that contains at least one heteroatom selected from S, O, N, or combinations thereof in an aromatic ring structure.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "aryloxy" refers to a monovalent group of formula —OAr where Ar is an aryl group.

As used herein, the term "aryloxycarbonyl" refers to a monovalent group of formula —(CO)OAr where Ar is an aryl group.

As used herein, the term "aryloxysulfonyl" refers to a monovalent group having the formula —SO$_3$Ar where Ar is an aryl group.

As used herein, the term "azo" refers to a divalent group of formula —N═N—.

As used herein, the term "carbonyl" refers to a divalent group of formula —(CO)— where the carbon atom is connected to the oxygen atom by a double bond.

As used herein, the term "carboxy" refers to a monovalent group of formula —(CO)OH.

As used herein, the term "conjugated" refers to unsaturated compounds having at least two carbon-carbon double or triple bonds with alternating carbon-carbon single bonds and carbon-carbon double or triple bonds.

As used herein, the term "cyano" refers to a group of formula —CN.

As used herein, the term "dialkylphosphonato" refers to a group of formula —(PO)(OR)$_2$ where R is an alkyl. As used herein the formula "(PO)" indicates that the phosphorus atom is attached to an oxygen atom with a double bond.

As used herein, the term "diarylphosphonato" refers to a group of formula —(PO)(OAr)$_2$ where Ar is an aryl.

As used herein, the term "electron donating" refers to a substituent that can donate electrons. Suitable examples include, but are not limited to, a primary amino, secondary amino, tertiary amino, hydroxy, alkoxy, aryloxy, alkyl, or combinations thereof.

As used herein, the term "electron withdrawing" refers to a substituent that can withdraw electrons. Suitable examples include, but are not limited to, a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

As used herein, the term "fluoroalkyl" refers to an alkyl group that has at least one hydrogen atom replaced with a fluorine atom.

As used herein, the term "formyl" refers to a monovalent group of formula —(CO)H where the carbon is attached to the oxygen atom with a double bond.

As used herein, the term "halo" refers to a halogen group (i.e., F, Cl, Br, or I). In some embodiments, the halo group is F or Cl.

As used herein, the term "halocarbonyl" refers to a monovalent group of formula —(CO)X where X is a halogen group (i.e., F, Cl, Br, or I).

As used herein, the term "heteroaryl" refers to a monovalent radical having a five to seven member aromatic ring that includes one or more heteroatoms independently selected from S, O, N, or combinations thereof in the ring. Such a heteroaryl ring can be connected to or fused to up to five ring structures that are aromatic, aliphatic, or combinations thereof. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, and indazolyl, and the like. A heteroaryl is a subset of a heterocyclic group.

As used herein, the term "heterocyclic" refers to a monovalent radical having a ring structure that is saturated or unsaturated and that includes one or more heteroatoms independently selected from S, O, N, or combinations thereof in the ring. The heterocyclic group can be a single ring, bicyclic, or can be fused to another cyclic or bicyclic group. The fused cyclic or bicyclic group can be saturated or unsaturated and can be carbocyclic or contain heteroatoms.

As used herein, the term "hydroxy" refers to a group of formula —OH.

As used herein, the term "mercapto" refers to a group of formula —SH.

As used herein, the term "perfluoroalkyl" refers to an alkyl group that has all the hydrogen atoms replaced with fluorine atoms. A perfluoroalkyl is a subset of a fluoroalkyl.

As used herein, the term "perfluoroalkylsulfonyl" refers to a monovalent group of formula —$SO_2R_f$ where $R_f$ is a perfluoroalkyl.

As used herein, the term "polymerization" refers to forming a higher weight material from monomer or oligomers. The polymerization reaction also can involve a cross-linking reaction.

As used herein when referring to a composition containing an initiator system and polymerizable material, the term "self-stable" means that the composition can be stored for at least one day without any visible gel formation at room temperature (i.e., 20° C. to 25° C.).

As used herein when referring to a compound, the term "oxidative stability" refers to the length of time needed to oxidize 50 weight percent of the compound ($t_{1/2}$) at room temperature (i.e., 20° C. to 25° C.) which can be calculated using pseudo-first order kinetics as described in K. A. Connors, *Chemical Kinetics: The Study of Reaction Rates in Solution*, Chapter 2, VCH, New York, 1990.

As used herein, the term "sulfo" refers to a group having the formula —$SO_3H$.

Compositions

A variety of materials are known for use as an electron donor in initiator systems for polymerization reactions. However, some of these materials have limited solubility in ethylenically unsaturated monomers. Further, some of these materials have limited oxidative stability, shelf-stability, or combinations thereof.

One aspect of the invention provides a composition that includes an electron donor and an electron acceptor. More specifically, the electron donor includes an arylsulfinate salt. The compositions can be used as initiator systems for free radical polymerization reactions. The initiator systems can be used in photopolymerization methods, thermal polymerization methods, or combinations thereof.

The electron donor has an oxidation potential in N,N-dimethylformamide of 0.0 to +0.4 volts versus a silver/silver nitrate reference electrode and is an arylsulfinate salt having an anion of Formula I $$Ar^1\text{—}SO_2^- \qquad\qquad\qquad I$$

and having a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group. The electron acceptor has a reduction potential in N,N-dimethylformamide of +0.4 to −1.0 volts versus a silver/silver nitrate reference electrode.

The electron donor is selected to have an oxidation potential and the electron acceptor is selected to have a reduction potential in a stated range. The oxidation and reduction potentials can be determined using cyclic voltammetry. As described herein, the oxidation and reduction potentials are measured by dissolving the compound of interest in a non-aqueous solvent (i.e., N,N-dimethylformamide) containing a supporting electrolyte (i.e., 0.1 moles/liter tetrabutylammonium hexafluorophosphate). The resulting solution is purged with an inert gas such as argon. A three-electrode configuration is used that includes a working electrode (i.e., a glassy carbon electrode), a reference electrode (i.e., a silver wire in a 0.01 moles/liter of silver nitrate dissolved in acetonitrile), and a counter electrode (i.e., a platinum wire). The oxidation or reduction potential is the voltage corresponding to the maximum current for the oxidation or reduction reaction.

One component of the composition is the electron donor. The electron donor is an arylsulfinate salt. The arylsulfinate salt is typically soluble in monomers capable of undergoing free radical polymerization reactions and in a variety of non-polar and polar solvents. As used herein, the term "soluble" refers to a compound that can be dissolved in an amount at least equal to 0.05 moles/liter, at least equal to 0.07 moles/liter, at least equal to 0.08 moles/liter, at least equal to 0.09 moles/liter, or at least equal to 0.1 moles/liter in a given material such as a solvent or monomer.

In some arylsulfinate salts, the $Ar^1$ group is a substituted phenyl or an unsubstituted or substituted $C_{7-30}$ aryl group having a carbocyclic aromatic ring. The aryl group can have a single carbocyclic aromatic ring or can have additional carbocyclic rings that are fused or connected to the carbocyclic aromatic ring. Any fused or connected rings can be saturated or unsaturated. The aryl often contains up to 5 rings, up to 4 rings, up to 3 rings, up to 2 rings, or one ring. The aryl group usually has up to 30 carbon atoms, up to 24 carbon atoms, up to 18 carbon atoms, up to 12 carbon atoms, or 6 carbon atoms. Examples of aryl groups having a single ring or multiple fused rings include, but are not limited to, phenyl, anthryl, naphthyl, acenaphthyl, phenanthryl, phenanthrenyl, perylenyl, and anthracenyl. A single bond, methylene group (i.e., —$C(R^b)_2$— where each $R^b$ is independently hydrogen, alkyl, or aryl), carbonyl group (i.e., —(CO)—), or combinations thereof can connect multiple rings. Examples of aryl groups having multiple connected rings include, but are not limited to, anthraquinonyl, anthronyl, biphenyl, terphenyl, 9,10-dihydroanthracenyl, and fluorenyl.

In other arylsulfinate salts, the $Ar^1$ group in Formula I can be an unsubstituted or substituted heteroaryl that has a five to seven member aromatic ring that contains one or more heteroatoms independently selected from S, O, N, or combinations thereof in the ring. The heteroaryl can have a single ring or can have multiple rings connected or fused together. Any additional connected or fused rings can be carbocyclic or contain a heteroatom and can be saturated or unsaturated. The heteroaryl group often has up to 5 rings, up to 4 rings, up to 3 rings, up to 2 rings, or one ring. The heteroaryl typically contains up to 30 carbon atoms. In some embodiments, the heteroaryl contains up to 20 carbon atoms, up to 10 carbon atoms, or up to 5 carbon atoms. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, azaphenanthrenyl, and indazolyl.

The $Ar^1$ group in Formula I, in some embodiments, can be substituted with an electron withdrawing group or an electron withdrawing group in combination with an electron donating group provided that the arylsulfinate salt has an oxidation potential in N,N-dimethylformamide of 0.0 to +0.4 volts versus a silver/silver nitrate reference electrode. Electron donating groups can be selected, for example, from a primary amino, secondary amino, tertiary amino, hydroxy, alkoxy, aryloxy, alkyl, or combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

In some embodiments, the $Ar^1$ group includes an electron withdrawing group that is conjugated to the sulfinate group. For example, the $Ar^1$ group can be a phenyl substituted with an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

Specific examples of the arylsulfinate anion of Formula I include, but are not limited to, 4-chlorobenzenesulfinate, 4-cyanobenzenesulfinate, 4-ethoxycarbonylbenzenesulfinate, 4-trifluoromethylbenzenesulfinate, 3-trifluoromethylbenzenesulfinate, 1-naphthalenesulfinate, 2-naphthalenesulfinate, and 1-anthraquinonesulfinate.

The arylsulfinate salts have a cation with at least one carbon atom and either a positively charged nitrogen atom or a positively charged phosphorus atom. In one embodiment, the cation of the arylsulfinate is of Formula II

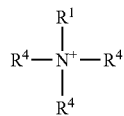

II where $R^1$ is an alkyl or aryl and each $R^4$ is independently a hydrogen, alkyl, or aryl. The $R^1$ and $R^4$ groups can be unsubstituted or substituted. An alkyl group can be substituted with a hydroxy. An aryl can be substituted with an alkyl, hydroxy, or combinations thereof.

In some examples of Formula II, $R^1$ and each $R^4$ group are independently a $C_{2-30}$ alkyl that is unsubstituted or substituted with a hydroxy. For example, $R^1$ and each $R^4$ independently can be an alkyl group having up to 20, up to 10, up to 8, up to 6, or up to 4 carbon atoms. The alkyl group often has at least 2, at least 3, at least 4, at least 6, or at least 8 carbon atoms. The alkyl group can have 4 to 30, 8 to 30, 3 to 10, 4 to 10, 4 to 8, or 4 to 6 carbon atoms in some compounds. In a specific example, the cation of the arylsulfinate salt is a tetrabutylammonium ion.

In other examples of Formula II, $R^1$ and two $R^4$ groups are each independently a $C_{2-30}$ alkyl that can be unsubstituted or substituted with a hydroxy. The remaining $R^4$ group is hydrogen. In still other examples, $R^1$ and one $R^4$ group are each independently a $C_{4-30}$ alkyl that is unsubstituted or substituted with a hydroxy; and the two remaining $R^4$ groups are hydrogen. In yet other examples, $R^1$ is a $C_{8-30}$ alkyl that is unsubstituted or substituted with a hydroxy; and the $R^4$ groups are hydrogen.

The $R^1$ group and each of the $R^4$ groups in Formula II independently can be an aryl group that is unsubstituted or substituted with an alkyl, hydroxy, or combinations thereof. An exemplary cation is tetraphenylammonium ion. In another example, $R^1$ and one $R^4$ are independently an aryl group that is unsubstituted or substituted with an alkyl, hydroxy, or combinations thereof; and the two remaining $R^4$ groups are hydrogen. An exemplary cation is diphenylammonium ion.

In other embodiments, the cation of the arylsulfinate salt is a ring structure that includes a 4 to 12 member heterocyclic group with a positively charged nitrogen atom. The heterocyclic group can be saturated or unsaturated and can contain up to three heteroatoms selected from nitrogen, oxygen, sulfur, or combinations thereof (i.e., there is one positively charged nitrogen atom and up to two other heteroatoms selected from nitrogen, oxygen, sulfur, or combinations thereof). The ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

The heterocyclic group in the cationic ring structure can be a single ring, bicyclic, or can be fused to another cyclic or bicyclic group. The fused cyclic or bicyclic group can be saturated or unsaturated and can have 0 to 3 heteroatoms. The ring structure can include up to 30 carbon atoms, up to 24 carbon atoms, up to 18 carbon atoms, up to 12 carbon atoms, up to 6 carbon atoms, or up to 4 carbon atoms and up to 6 heteroatoms, up to 4 heteroatoms, up to 2 heteroatoms, or 1 heteroatom. In some embodiments, the ring structure is a 4 to 12 member heterocyclic group that is a fused to an aromatic ring having 0 to 3 heteroatoms.

Suitable examples of five member heterocyclic groups that contain a positively charged nitrogen atom include, but are not limited to, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, and oxathiazolium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is an imidazolium ion or oxazolium ion that is unsubstituted or substituted.

The five member heterocyclic groups can be fused to another cyclic group. In some exemplary ring structures, a five membered heterocyclic group is fused to an aromatic group. Exemplary ring structures include, but are not limited to, an indole ion, indazolium ion, benzopyrrolidinium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, carbozolium ion, and purinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is a benzoxazolium ion or a benzothiazolium ion that is unsubstituted or substituted.

Suitable examples of six member heterocyclic groups that contain a positively charged nitrogen atom include, but are not limited to, a pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof. In some applications, the cation is a pyridinium ion or a morpholinium ion that is unsubstituted or substituted.

The six member heterocyclic groups can be fused to another cyclic group. In some exemplary ring structures, a six membered heterocyclic group is fused to an aromatic group. Exemplary ring structures include, but are not limited to, isoquinolinium ion, quinolinium ion, cinnolinium ion, quinazolinium ion, benzopyrazinium ion, benzopiperazinium ion, benzotriazinium ion, benzoxazinium ion, benzopiperidinium ion, benzoxathiazinium ion, benzoxadizinium ion, benzomorpholinium ion, naphtyridinium ion, and acridinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof.

Suitable examples of seven member heterocyclic groups that contain a positively charged nitrogen atom include, for example, an azepinium ion and diazepinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

Examples of heterocyclic groups that are bicyclic include, but are not limited to, N-alkylated or N-protonated 1,4-diazabicyclo [2.2.2] octane and N-alkylated or N-protonated 1-azabicyclic [2.2.2] octane that is unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

In other embodiments, the cation of the arylsulfinate salt contains a positively charged phosphorus atom of Formula III

where each $R^2$ is independently an alkyl or aryl that is unsubstituted or substituted. An alkyl group can be substituted with a hydroxy. An aryl can be substituted with an alkyl, hydroxy, or combinations thereof.

In some examples of Formula III, all of the $R^2$ groups are an aryl group. For example, the cation can be a tetraphenylphosphonium ion. In other examples, one, two, or three of the $R^2$ groups are an aryl with the remaining $R^2$ group or groups being a $C_{2-30}$ alkyl.

Some of the arylsulfinate salts can have an anion of Formula IV

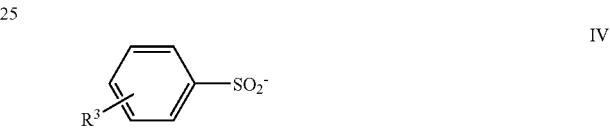

and a cation that contains a positively charged nitrogen atom. In Formula IV, $R^3$ can be in an ortho, para, or meta position of the benzene ring and is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or aminocarbonyl. In some compounds, $R^3$ is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, or alkylsulfonyl. In other compounds, $R^3$ is a halo, cyano, or alkoxycarbonyl group.

Specific examples Formula IV where $R^3$ is located in the para position of the phenyl ring include 4-cyanobenzenesulfinate, 4-chlorobenzenesulfinate, 4-ethoxycarbonylbenzenesulfinate, and 4-trifluoromethylbenzenesulfinate. A specific example of $R^3$ located in the meta position of the phenyl ring includes 3-trifluoromethylbenzenesulfinate.

For some applications, the arylsulfinate salt includes an anion of Formula IV and a cation that is a tetraalkyammonium ion. The alkyl groups of the tetraalkylammonium ion can be the same or different and typically contain 2 to 30 carbon atoms. For example, the alkyl groups can contain 4 to 30 carbon atoms, 8 to 30 carbon atoms, 3 to 10 carbon atoms, 4 to 10 carbon atoms, 4 to 8 carbon atoms, or 4 to 6 carbon atoms. Specific arylsulfinate salts include, but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, and tetrabutylammonium 3-trifluoromethylbenzenesulfinate.

Other specific examples of electron donors include, but are not limited to, tetrabutylammonium 1-naphthalenesulfinate, tetrabutylammonium 2-naphthalenesulfinate, and tetrabutylammonium 1-anthraquinonesulfinate, 1-ethyl-3-methylimidazolium 4-cyanobenzenesulfinate, N,N-dimethylmorpholinium 4-cyanobenzenesulfinate, 3-ethyl-2-methylbenxoxazolium 4-cyanobenzenesulfinate, 1-methyl-4-aza-1-azoniabicyclo[2.2.2]octane 4-cyanobenzenesulfinate, and N-hexadecylpyridinium 4-cyanobenzenesulfinate.

In some embodiments, the arylsulfinates can be stored as a neat compound at room temperature without undergoing oxidative degradation. For example, some of the arylsulfinates can be stored for greater than one day, greater than 2 days, greater than 1 week, greater than 2 weeks, or greater than 1 month. The time required at room temperature (i.e., 20° C. to 25° C.) to oxidize 50 percent of the compound ($t_{1/2}$) can be used to compare the relative ease of oxidative degradation of various arylsulfinates. The $t_{1/2}$ is calculated based on pseudo-first order kinetics as described in K. A. Connors, *Chemical Kinetics: The Study of Reaction Rates in Solution*, Chapter 2, VCH, New York, 1990.

The arylsulfinate salt has an oxidation potential in N,N-dimethylformamide of +0.4 to 0.0 volts versus a silver/silver nitrate reference electrode. In some embodiments, the electron donor has an oxidation potential in N,N-dimethylformamide of +0.08 to 0.3 volts or +0.08 to +0.2 volts versus a silver/silver nitrate reference electrode.

Another component of the compositions is an electron acceptor having a reduction potential in N,N-dimethylformamide of +0.4 to −1.0 volts versus a silver/silver nitrate reference electrode. In some embodiments, the electron acceptor has a reduction potential in N,N-dimethylformamide of +0.1 to −1.0 volts, 0.0 to −1.0 volts, −0.1 to −1.0 volts, or −0.5 to −1.0 volts versus a silver/silver nitrate reference electrode.

Suitable electron acceptors include, but are not limited to, metal ions in an oxidized state, persulfates, peroxides, iodonium salts, hexaarylbisimidazoles, or combinations thereof. In some applications, the electron acceptor is selected to be soluble in monomers capable of undergoing free radical polymerization reactions.

The electron acceptor is usually not mixed with the electron donor prior to use in an initiator system if the electron acceptor is a metal ion in an oxidized state, a peroxide, a persulfate, or combinations thereof. These electron acceptors can often react with the electron donor at room temperature (i.e., 20° C. to 25° C.) or at an elevated temperature (e.g., up to 150° C.) within a relatively short period of time (e.g., less than 1 hour, less than 30 minutes, less than 10 minutes, or less than 5 minutes). Initiator systems containing metal ions in an oxidized state, peroxides, or persulfates typically do not require a sensitizing compound to activate the initiator system. Such initiator systems can be initiated without activation by actinic radiation (i.e., the initiator systems are thermal systems).

Suitable electron acceptor metal ions include, for example, ions of group III metals, transition metals, and lanthanide metals. Specific metal ions include, but are not limited to, Fe(III), Co(III), Ag(I), Ag(II), Cu(II), Ce(III), Al(III), Mo(VI), and Zn(II). Suitable electron acceptor peroxides include benzoyl peroxide, lauryl peroxide, and the like. Suitable electron acceptor persulfates include, for example, ammonium persulfate, tetraalkylammonium persulfate (e.g., tetrabutylammonium persulfate), and the like.

In some embodiments, the electron acceptor does not include metal ions in an oxidized state, peroxides, or persulfates. For example, if the initiator system is used in a photopolymerization method (i.e., the initiator is a photoinitiator system), the electron acceptor typically is selected so that it does not react directly with the electron donor at room temperature. The electron acceptor and the electron donor typically can be stored together for at least one day prior to activation of the photoinitiator system by excitation of a sensitizing compound. Electron acceptors suitable for photopolymerization reactions include, but are not limited to, iodonium salts, hexaarylbisimidazoles, or combinations thereof. In some photoinitiator systems, hydroxy-containing materials are added to enhance the storage stability.

In some applications, particularly applications that use a photoinitiator system, the electron donor has a reduction potential in N,N-dimethylformamide of +0.1 to −1.0 volts, 0.0 to −1.0 volts, −0.1 to −1.0 volts, or −0.5 to −1.0 volts versus a silver/silver nitrate reference electrode. Electron acceptors having such reduction potentials include iodonium salts. The iodonium salts are often diaryliodonium salts. Diaryliodonium salts can be combined with an arylsulfinate salt and polymerizable material to form a stable composition.

Suitable iodonium salts are described in further detail in U.S. Pat. Nos. 3,729,313; 3,741,769; 3,808,006; 4,250,053; 4,394,403; 5,545,676; and 5,998,495, the iodonium salt disclosures of which are incorporated herein by reference. The iodonium salt can be a simple salt, a metal complex salt, or combinations thereof. Examples of simple salts include those having an anion such as a halide, sulfonate, carboxylate, or combinations thereof. Examples of metal complex salts include those having an anion such as hexafluorophosphate, hexafluoroarsenate, hexafluoroantimonate, pentafluorohydroxyantimonate, tetrafluoroborate, tetra(pentafluorophenyl)borate, or combinations thereof.

The iodonium metal complex salts can be prepared by metathesis of corresponding iodonium simple salts (such as, for example, diphenyliodonium chloride or diphenyliodonium bisulfite) in accordance with the teachings of Beringer et al., *J. Am. Chem. Soc.*, 81, 342 (1959). In a specific example, the metal complex salt diphenyliodonium tetrafluoroborate can be prepared by the addition of an aqueous solution containing silver fluoroborate, fluoroboric acid, and phosphorous acid to an aqueous solution of diphenyliodonium chloride. The silver halide that precipitates can be filtered off and the filtrate concentrated to yield diphenyliodonium tetrafluoroborate that may be purified by recrystallization.

The diaryliodonium simple salts can be prepared in accordance with Beringer et al., above, by various methods including coupling of two aromatic compounds with iodyl sulfate in sulfuric acid; coupling of two aromatic compounds with an iodate in acetic acid-acetic anhydride; coupling of two aromatic compounds with an iodine acrylate in the presence of an acid; or condensation of an iodoso compound (e.g., iodoso diacetate) or an iodoxy compound with another aromatic compound in the presence of an acid.

Exemplary diaryliodonium salts include diphenyliodonium chloride, diphenyliodonium tetrafluoroborate, di(4-methylphenyl)iodonium tetrafluoroborate, phenyl-4-methylphenyliodonium tetrafluoroborate, di(4-heptylphenyl)iodonium tetrafluoroborate, phenyl-4-heptylphenyliodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, diphenyliodonium hexafluorophosphate, di(4-methylphenyl)iodonium hexafluorophosphate, diphenyliodonium hexafluoroarsenate, di(4-phenoxyphenyl)iodonium tetrafluoroborate, phenyl-2-thienyliodonium hexafluorophosphate, 3,5-dimethylpyrazolyl-4-phenyliodonium hexafluorophosphate, diphenyliodonium hexafluoroantimonate, 2,2'-diphenyliodonium tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methodycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, diphenyliodonium hexafluoroantimonate, and diphenyliodonium tetra(pentafluorophenyl)borate.

In some applications, the electron acceptor is diphenyliodonium chloride, diphenyliodonium hexafluorophosphate, diphenyliodonium tetrafluoroborate, diphenyliodonium hexafluoroantimonate, diphenyliodonium tetra(pentafluorophenyl)borate, or combinations thereof. These electron acceptors tend to promote faster reactions and to be more soluble in inert organic solvents compared to some other iodonium salts.

The initiator system can include a hexaarylbisimidazole compound as the electron acceptor. Such compounds can be synthesized as described in *J. Org. Chem.*, 36, 2762 (1971). A hexaarylbisimidazole is commercially available under the trade designation SPEEDCURE BCIM from Lambson, West Yorkshire, England.

For compositions that are a photoinitiator system, a solution that is colorless to the eye is often formed when the electron acceptor is dissolved in a suitable solvent such as an alcohol or in an ethylenically unsaturated monomer. A solution of the electron acceptor in an alcohol typically does not absorb in the visible region of the electromagnetic spectra. That is, the molar extinction coefficient of the electron acceptor can be less than 100 or less than 50 $l\text{-mole}^{-1}\text{cm}^{-1}$ at 350 nm.

The oxidation potential of the electron donor can be greater than, equal to, or less than the reduction potential of the electron acceptor. In some embodiments, the oxidation potential of the arylsulfinate salt is more positive than the reduction potential of the electron acceptor. Such compositions tend to have low reactivity in the presence of a monomer capable of undergoing a free radical polymerization reaction at room temperature or in the absence of actinic radiation. In other embodiments, the reduction potential of the electron acceptor is more positive than the oxidation potential of the arylsulfinate salt. Such compositions tend to be reactive upon mixing in the presence of a monomer capable of undergoing a free radical polymerization reaction. The reactivity also can be influenced by other factors such as concentration of the arylsulfinate salt and the electron acceptor, temperature, and the nature of the other components in the curable composition (e.g., the presence of hydroxy-containing compounds can decrease the reactivity of the composition).

The composition can further include a sensitizing compound. The addition of a sensitizing compound allows the composition to be used as an initiator system for photopolymerization methods. Actinic radiation can be used to form an excited sensitizing compound. The electron donor can donate an electron to the excited sensitizing compound to form a reduced sensitizing compound that is a radical anion. This radical anion can donate an electron to an electron acceptor to yield an initiating free radical. The sensitizing compound can be a dye, pigment, or combinations thereof.

Suitable sensitizing compounds that are dyes include, but are not limited to, ketones (e.g., monoketones and diketones), coumarin dyes (e.g., ketocoumarins such as Coumarin 153), xanthene dyes (e.g., Rose Bengal and Rhodamine 6G), acridine dyes, thiazole dyes, thiazine dyes (e.g., Methylene Blue and Methylene Violet), oxazine dyes (e.g., Basic Blue 3 and Nile Blue Chloride), azine dyes (e.g., Methyl Orange), aminoketone dyes, porphyrins (e.g., porphyrazine), aromatic polycyclic hydrocarbons, p-substituted aminostyryl ketone compounds, aminotriaryl methanes, cyanine dyes (e.g., the cyanine dye described in *Biochemistry*, 12, 3315 (1974)), squarylium dyes, pyridinium dyes, benzopyrilium dyes, and triarylmethane (e.g., Malachite Green). In some applications, the sensitizing compounds include xanthenes, monoketones, diketones, or combinations thereof. Other suitable sensitizing dyes are described in F. J., Green, *The Sigma-Aldrich Handbook of Stains, Dyes, and Indicators*, Aldrich Chemical Company, Inc., Milwaukee, Wis. (1990).

In some embodiments, the sensitizing compound is a xanthene dye such as fluorosceins, rhodamines, eosins, and pyronins.

Exemplary monoketones include 2,2-dihydroxybenzophenone, 4,4-dihydroxybenzophenone, 2,4-dihydroxybenzophenone, di-2-pyridyl ketone, di-2-furanyl ketone, di-2-mercaptophenyl ketone, benzoin, fluorenone, chalcone, Michler's ketone, 2-fluoro-9-fluorenone, 2-chloromercaptoxanthone, acetophenone, benzophenone, 1- or 2-acetonaphthone, 9-acetylanthracene, 2-, 3-, or 9-acetylphenanthrene, 4-acetylbiphenyl, propiophenone, n-butyrophenone, valerophenone, 2-, 3-, or 4-acetylpyridine, 3-acetylcoumarin, and the like.

Exemplary diketones include aralkyldiketones such as anthraquinone, phenanthrenequinone, o-, m-, and p-diacetylbenzene, 1,3-, 1,4-, 1,5-, 1,6-, 1,7-, and 1-8 diacetylnaphthalene, 1,5-, 1,8-, and 9,10-diacetylanthracene, and the like. Exemplary alpha-diketones include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-, 3,3'-, and 4,4'-dihydroxybenzil, furil, di-3,3'-indolylethanedione, 2,3-bornanedione (camphorquinone), biacetyl, 1,2-cyclohexanedione, 1,2-naphthaquinone, acenaphthaquinone, and the like.

The dye can have a molar extinction coefficient up to about 150,000 $l\text{-mole}^{-1}\text{cm}^{-1}$. In some applications, the dye has a molar extinction coefficient that is up to 85,000 $l\text{-mole}^{-1}\text{cm}^{-1}$, up to 70,000, up to 50,000, up to 30,000, up to 10,000, or up to 5,000 $l\text{-mole}^{-1}\text{cm}^{-1}$.

For applications requiring deep cure (e.g., cure of highly filled composites such as dental composites or cure of a thick sample), a sensitizing compound is typically selected that has an extinction coefficient less than 1000 $l\text{-mole}^{-1}\text{cm}^{-1}$. In some examples, the extinction coefficient at the wavelengths of actinic radiation used for photopolymerization is less than 500 or less than 100 $l\text{-mole}^{-1}\text{cm}^{-1}$. The alpha-diketones, for example, are sensitizing compounds that can be used for such applications.

The sensitizing compound also can be a pigment as described in U.S. Pat. Nos. 4,959,297 and 4,257,915, the disclosures of which are incorporate herein by reference in their entirety. Suitable inorganic pigments include, but are not limited to, titanium dioxide, strontium titanate, barium titanate, zinc oxide, zinc sulfide, zinc selenide, cadmium sulfide, cadmium selenide, cadmium telluride, or combinations thereof. Suitable organic pigments include, but are not limited to, phthalocyanine blue (pigment blue 15), copper polychlorophthalocyanine green (pigment green 7), copper polybromochlorophthalocyanine (pigment green 36), perylene scarlet (vat red 29), perylene vermillion (pigment red 23), perylene maroon, perylene Bordeaux, perylene dianhydride (perylene red), and those described in "Pigments-Inorganic" and "Pigments-Organic" in *Kirk-Othmer Encyclopedia of Chemical Technology*, Third ed., Volume 17, pp. 788–817, John Wiley and Sons, New York, 1982. The organic pigments also can be semiconducting polymers as described by Y. M. Paushkin et al., *Organic Polymeric Semiconductors*, John Wiley & Sons, New York, 1974 and by J. M. Pearson, *Pure and Appl. Chem.*, 49, 463–477 (1977).

The composition can further include monomers that can be polymerized using a free-radical polymerization reaction. The monomers typically contain at least one ethylenically-unsaturated double bond. The monomers, for example, can be monoacrylates, diacrylates, polyacrylates, monomethacrylates, dimethacrylates, polymethacrylates, or combinations thereof. The monomers can be unsubstituted or substituted with a hydroxy. Exemplary monomers include methyl acrylate, methyl methacrylate, ethyl acrylate, ethyl methacrylate, isopropyl acrylate, isopropyl methacrylate, n-hexyl acrylate, stearyl acrylate, allyl acrylate, glycerol acrylate, glycerol diacrylate, glycerol triacrylate, ethyleneglycol diacrylate, diethyleneglycol diacrylate, triethyleneglycol diacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane, and tris-hydroxyethyl-isocyanurate trimethylacrylate. The monomers also can be bis-acrylates and bis-methacrylates of polyethylene glycol having an average molecular weight ($M_n$) of 200 to 500; copolymerizable mixtures of acrylated monomers such as those described in U.S. Pat. No. 4,652,274, incorporated herein by reference in its entirety; acrylated monomers such as those described in U.S. Pat. No. 4,642,126, incorporated herein by reference in its entirety; unsaturated amides such as methylene bis-arylamide, methylene bis-methacrylamide, 1,6-hexamethylene bis-acrylamide, diethylene triamine tris-acrylamide, and beta-methacrylaminoethyl methacrylate; and vinyl monomers such as styrene, diallyl phthalate, divinyl succinate, divinyl adipate, and divinylphthalate. Mixtures of two or more monomers can be used, if desired.

Some compositions, such as those that undergo photopolymerization reactions, can include a hydroxy-containing material. The hydroxy-containing material can improve the storage stability of some compositions. Hydroxy-containing material, for example, can be an alcohol, a hydroxy-containing monomer, or combinations thereof.

Suitable alcohols include, but are not limited to, methanol, ethanol, 1-propanol, 2-propanol, 2-methyl-2-propanol, 1-butanol, 2-butanol, 1-pentanol, neopentyl alcohol, 3-pentanol, 1-hexanol, 1-heptanol, 1-octanol, 2-phenoxyethanol, cyclopentanol, cyclohexanol, cyclohexylmethanol, 3-cyclohexyl-1-propanol, 2-norbornanemethanol, and tetrahydrofurfuryl alcohol.

The alcohol can be a diol or a polyol. Suitable diols include materials ranging in size from ethylene glycol to a polyethylene glycol. Exemplary diols and polyols include, but are not limited to, 1,2-ethanediol, 1,2-propanediol, 1,3-propanediol, 1,4-butanediol, 1,3-butanediol, 2-methyl-1,3-propanediol, 2,2-dimethyl-1,3-propanediol, 2-ethyl-1,6-hexanediol, 1,5-pentanediol, 1,6-hexanediol, 1,8-octanediol, neopentyl glycol, glycerol, trimethylolpropane, 1,2,6-hexanetriol, trimethylolethane, pentaerythritol, quinitol, mannitol, sorbitol, diethylene glycol, triethylene glycol, tetraethylene glycol, glycerine, 2-ethyl-2-(hydroxymethyl)-1,3-propanediol, 2-ethyl-1,3-pentanediol, 1,4-cyclohexanedimethanol, and 1,4-benzene-dimethanol. Other useful polyols are disclosed in U.S. Pat. No. 4,503,211, the disclosure of which is incorporated herein by reference.

Higher molecular weight polyols include the polyethylene oxide and polypropylene oxide polymers in the molecular weight ($M_n$) range of 200 to 20,000 such as polyethyleneoxide materials available from Dow Chemical Co., Midland, Mich. under the trade designation CARBOWAX; carpolactone polyols in the molecular weight ($M_n$) range of 200 to 5,000 such as polyol materials available from Dow Chemical Co., Midland, Mich. under the trade designation TONE; polytetramethylene ether glycol in the molecular weight ($M_n$) range of 200 to 4,000 such as the materials available from DuPont, Wilmington, Del. under the trade designation TERATHANE and from BASF, Mount Olive, N.J. under the trade designation POLYTHF 250; polyethylene glycol such as material available from Dow Chemical Co., Midland, Mich. under the trade designation PEG 200; hydroxy-terminated polybutadiene resins such as materials from Atofina, Philadelphia, Pa. under the trade designation POLYBD; phenoxy resins such as those commercially available from Phenoxy Associates, Rock Hill, S.C.; and similar materials supplied by other manufacturers.

Suitable hydroxy-containing monomers include hydroxy substituted esters of acrylic acid or hydroxy substituted esters of methacrylic acid. Exemplary hydroxy-containing monomers include 2-hydroxyethylacrylate, 2-hydroxyethylmethacrylate, 4-hydroxybutylactylate, 4-hydroxybutylmethacrylate, glycerol acrylate, glycerol diacrylate, glycerol methacrylate, glycerol dimethacrylate, and the like. In some applications, all of the monomers are hydroxy-containing materials.

The components of the initiator system can be present in an amount effective to enable free radical polymerization of the ethylenically-unsaturated monomers. The amount of the electron donor and the electron acceptor can affect the kinetics of the polymerization reaction and the shelf life of the composition. The rate of the reaction typically increases with an increased concentration of the electron acceptor and electron donor. The shelf life typically shortens with higher levels of the electron donor and electron acceptor.

In some applications, the electron donor and the electron acceptor can each be present in an amount up to 4 weight percent based on the weight of the monomer. The amount of the electron donor and the electron acceptor can be the same or different. In some embodiments, the electron donor and the electron acceptor are each present in an amount up to 3 weight percent, up to 2 weight percent, up to 1 weight percent, or up to 0.5 weight percent based on the weight of the monomers. For example, the electron donor and the electron acceptor can each be present in an amount of 0.1 to 4 weight percent, 0.1 to 3 weight percent, 0.1 to 2 weight percent, or 0.5 to 1 weight percent based on the weight of the monomers.

The sensitizing compound, if present, is often used in an amount up to 4 weight percent based on the weight of the monomer. In some applications, the sensitizing compound is present in an amount up to 3 weight percent, up to 2 weight percent, up to 1 weight percent, or up to 0.5 weight percent based on the weight of the monomers. For example, the sensitizing compound can be present in an amount of 5 ppm to 4 weight percent, 10 ppm to 2 weight percent, 15 ppm to 1 weight percent, or 20 ppm to 0.5 weight percent based on the weight of the monomers.

The compositions can contain a wide variety of additives depending on the desired use of the polymerized material. Suitable additives include solvents, diluents, resins, binders, plasticizers, inorganic and organic reinforcing or extending fillers, thixotropic agents, UV absorbers, medicaments, and the like.

In some embodiments, the components of the compositions can be selected to provide a useful combination of cure speed, cure depth, and shelf life. Some compositions can cure well even when loaded with large amounts of fillers. The compositions can be used to form foams, shaped articles, adhesives, filled or reinforced composites, abrasives, caulking and sealing formulations, casting and molding formulations, potting and encapsulating formulations, impregnating and coating formulations, and the like.

Suitable applications for the compositions include, but are not limited to, graphic arts imaging (e.g., for color proofing systems, curable inks, and silverless imaging), printing plates (e.g., for projection plates and laser plates), photoresists, solder masks for printed circuit boards, coated abrasives, magnetic media, photocurable adhesives (e.g., for orthodontics and general bonding applications), and photocurable composites (e.g., for autobody repair and dental restoratives), protective coatings, and abrasion resistant coatings. The compositions are also suitable for use in a multi-photon process, where high intensity/short pulse lasers are used in combination with suitable dyes and co-reactants to produce polymerizable compositions that are useful for imaging, microreplication, and stereolithographic applications. The compositions can be used in other applications that are known to those skilled in the art.

Polymerization Methods

The invention also provides methods for polymerizing ethylenically unsaturated monomers using free radical polymerization reactions. The methods can be photopolymerization methods, thermal polymerization methods, or combinations thereof.

The photopolymerization method includes irradiating a photopolymerizable composition with actinic radiation until the photopolymerizable composition gels or hardens. The photopolymerizable composition includes a photoinitiator system and monomers capable of undergoing free radical polymerization reactions (i.e., ethylenically unsaturated monomers). Three components are typically used in the photoinitiator system: an electron donor, an electron acceptor, and a sensitizing compound. In some embodiments of the photopolymerization method, the photopolymerizable composition can be mixed together and stored for at least one day prior to use.

The electron donor in the photoinitiator system has an oxidation potential in N,N-dimethylformamide of 0.0 to +0.4 volts versus a silver/silver nitrate reference electrode and includes an arylsulfinate salt having an anion of Formula I

  $\quad\quad\quad\quad\quad$ I and a cation that contains at least one carbon atom and either a positively charged nitrogen atom or a positively charged phosphorus atom. The $Ar^1$ group in Formula I is a substituted phenyl, an unsubstituted or substituted $C_{7-30}$ aryl, or an unsubstituted or substituted $C_{3-30}$ heteroaryl. A substituted $Ar^1$ group can have a substituent that is an electron withdrawing group or an electron withdrawing group in combination with an electron donating group.

The electron acceptor in N,N-dimethylformamide usually has a reduction potential in the range of +0.4 to −1.0 volts versus a silver/silver nitrate reference electrode. In some embodiments, the electron acceptor has a reduction potential in N,N-dimethylformamide of +0.1 to −1.0 volts, 0.0 to −1.0 volts, −0.1 to −1.0 volts, or −0.5 to −1.0 volts versus a silver/silver nitrate reference electrode. Suitable electron acceptors for photopolymerization methods are often selected to not react directly with the arylsulfinate electron donors, at least at room temperature. A solution of the electron acceptor dissolved in a suitable solvent such as an alcohol or dissolved in an ethylenically unsaturated monomer is typically colorless to the eye. Exemplary electron acceptors include hexaarylbisimidazoles and diaryliodonium salts.

The photopolymerizable compositions can include a wide variety of different types of sensitizing compounds such as dyes, organic pigments, inorganic pigments, or combinations thereof. In some embodiments, the sensitizing compound can change colors indicating that the polymeric material has been cured. The color changes can be attributed to chemical alterations to the sensitizing compound.

The photoinitiator system can be activated by exposing the sensitizing compound to actinic radiation having a wavelength in the range of 250 to 1000 nanometers. In some applications, the actinic radiation has a wavelength in the range of 300 to 1000 nanometers, in the range of 350 to 1000 nanometers, in the range of 250 to 850 nanometers, in the range of 250 to 800 nanometers, in the range of 400 to 800 nanometers, in the range of 425 to 800 nanometers, or in the range of 450 to 800 nanometers. The electron donor can donate electrons to the excited sensitizing compound. The sensitizing compound can be reduced and the electron donor can be oxidized. The reduced sensitizing compound is a radical anion that can donate an electron to an electron acceptor to yield an initiating free radical for the polymerization reaction. That is, the initiating free radical is the reduced electron acceptor. In some instances, the oxidized electron donor is a radical species that also can function as an initiating free radical for the polymerization reaction.

Monomers suitable for photopolymerization methods typically include an ethylenically unsaturated monomer such as a monoacrylate, monomethacrylate, diacrylate, dimethacrylate, polyacrylate, polymethacrylate, or combinations thereof. In some applications, at least some of the monomers are hydroxy-containing monomers such as hydroxy substituted esters of acrylic acid or hydroxy substituted esters of methacrylic acid.

The photopolymerizable composition with a photoinitiator system typically includes a hydroxy-containing material. Suitable hydroxy-containing materials include, for example, alcohols, hydroxy-containing monomers, or combinations thereof. The amount of hydroxy-containing material can alter the amount of time that the polymerizing composition can be stored prior to use. The storage stability often increases with an increase in the amount of hydroxy-containing material in the photopolymerizable composition. In some applications, the photopolymerizable composition includes no less than 5 weight percent, no less than 10 weight percent, no less than 20 weight percent, no less than 30 weight percent, or no less than 40 weight percent hydroxy-containing materials based on the weight of the photopolymerizable composition.

In some embodiments, visible light can be used to excite the sensitizing compound and activate the photopolymerizable composition. This can be advantageous because relatively inexpensive light sources can be used. Light sources emitting in the visible region of the electromagnetic spectrum tend to be less expensive than those emitting, for example, in the ultraviolet region. Other light sources that include ultraviolet radiation or a combination of ultraviolet and visible radiation also can be used. Typical light sources include, but are not limited to, mercury vapor discharge lamps, carbon arcs, tungsten lamps, xenon lamps, sunlight, lasers, light emitting diodes, and the like.

The invention also provides a method of polymerization that includes forming a polymerizable composition and reacting the polymerizable composition. The polymerizable composition includes an ethylenically unsaturated monomer, an electron donor having an oxidation potential in N,N-dimethylformamide of 0.0 to +0.4 volts versus a silver/silver nitrate reference electrode, and an electron acceptor having a reduction potential in N,N-dimethylformamide of +0.4 to −1.0 volts versus a silver/silver nitrate reference electrode. The electron donor includes an arylsulfinate salt having an anion of Formula I

Ar$^1$—SO$_2^-$     I and having a cation that contains at least one carbon atom and either a positively charged nitrogen atom or a positively charged phosphorus atom. The Ar$^1$ group in Formula I is a substituted phenyl, an unsubstituted or substituted C$_{7-30}$ aryl, or an unsubstituted or substituted C$_{3-30}$ heteroaryl. A substituted Ar$^1$ group can have a substituent that is an electron withdrawing group or an electron withdrawing group in combination with an electron donating group.

In thermally initiated free radical polymerization reactions, the electron acceptor is often selected to react directly with the electron donor resulting in the formation of a reduced electron acceptor. The reduced electron acceptor can be a radical that functions as an initiating free radical for the polymerization reaction. The reaction between the electron donor and acceptor can occur at room temperature (i.e., 20° C. to 25° C.) or at elevated temperatures (e.g., temperatures up to 150° C.). The electron acceptor and the electron donor are typically kept in separate containers (i.e., not mixed together) until polymerization is desired.

Suitable electron acceptors include metal ions in an oxidized state, peroxides, and persulfates. No sensitizing compound is typically needed to activate the initiator system. However, a sensitizing compound can be added, if desired, to accelerate the reactivity in the presence of actinic radiation.

Any ethylenically unsaturated monomer can be used. The monomer is typically a monoacrylate, monomethacrylate, diacrylate, dimethacrylate, polyacrylate, polymethacrylate, or combinations thereof. The monomers can be unsubstituted or substituted with hydroxy groups.

EXAMPLES

Unless otherwise noted, as used herein:

the solvents and reagents were or can be obtained from Aldrich Chemical Co., Milwaukee, Wis. or may be synthesized by known methods;

electrochemical instrumentation for cyclic voltammetry was obtained from Princeton Applied Research, Oak Ridge, Tenn.;

N,N-dimethylformamide was obtained from EM Science, Gibbstown, N.J.;

4-(trifluoromethyl)benzenesulfonyl chloride was obtained from Alfa Aesar, Ward Hill, Mass.;

the term "emim" refers to the 1-ethyl-3-methylimidazolium cation;

the term "4-HBA" refers to 4-hydroxybutyl acrylate;

the term "HEA" refers to 2-hydroxyethyl acrylate;

the term "KL68 Dye" refers to the dye bis-[4-(diphenylamino)stryl]-1-(2-ethylhexyloxy),4-(methoxy)benzene;

the term "Cyanine 1" refers to 3-methyl-2-[5-(3-methyl-2-benzothiazolinylidene)-1,3-pentadienyl]benzothiazolium iodide and was prepared according to the general method disclosed in Biochemistry, 13 (42), 3315–3330 (1974);

the term "SR339" refers to 2-phenoxyethyl acrylate and was obtained from Sartomer Co. Inc., Exton, Pa.;

the term "SR238" refers to 1,6-hexanediol diacrylate and was obtained from Sartomer Co. Inc., Exton, Pa.;

the term "SR399" refers to pentaerythritol pentaacrylate and was obtained from Sartomer Co. Inc., Exton, Pa.;

the term "SR351" refers to trimethylolpropane triacrylate which was obtained from Sartomer Co., Inc., Exton, Pa.;

the term "IR140" refers to 5,5'-dichloro-11-diphenylamino-3,3'-diethyl-10,12-ethylenethiatricarobocyanine perchlorate; and the term "IR780 iodide" refers to 2-[2-[2-chloro-3-[(1,3-dihydro-3,3-dimethyl-1-propyl-2H-indol-2-ylidene)ethylidene]-1-cyclohexen-1-yl]ethenyl]-3,3-dimethyl-1-propylindolium iodide.

Methods

Measurement of Oxidation Potentials

The electrochemical measurements of the exemplary arylsulfinates were made using an EG&G PARC Model 175 Universal Programmer, interfaced to a Princeton Applied Research Model 173 potentiostat/galvanostat fitted with a Princeton Applied Research Model 179 Digital Coulometer and Model 178 Electrometer. The signal was digitized using a Model DI-151R5 Waveform Recording System (available from DATAQ Instruments, Inc., Akron, Ohio) and then stored and analyzed on a Dell OptiPlex XM 590 pc. Scans were run at 100 mV/sec scan rate.

The electrochemical measurements were made using a three-electrode configuration: a reference electrode, a working electrode, and a counter electrode. The reference electrode was a fritted electrode (obtained from Sargent Welch, Buffalo Grove, Ill.) that was filled with 0.01M AgNO$_3$ in acetonitrile and fitted with a silver wire 1 mm in diameter by approximately 19 cm in length. The counter electrode was a platinum wire 1.0 mm in diameter and approximately 16 cm long (overall length) formed into a coil having a coil diameter of approximately 10 mm and a coil length of about 7.5 cm. The working electrode was a glassy carbon electrode, approximately 3.5 mm in diameter (obtained from BAS, Inc., West Lafayette, Ind.). The glassy carbon electrode was polished using first a 3.0 micron aluminum oxide powder/deionized water slurry, then a 0.3 micron alpha alumina powder/deionized water slurry. The polishing powders were obtained from Buehler LTD, Evanston, Ill.

The cell was a 50 mL four neck round bottom flask. Each electrode was sealed in the flask using the appropriately sized rubber septum. The fourth inlet was used to introduce an argon purge to remove oxygen and keep atmospheric moisture out of the cell.

The supporting electrolyte was tetrabutylammonium hexafluorophosphate (TBA PF$_6$) (obtained from Southwestern Analytical Chemicals, Inc., Austin, Tex.). The TBA PF$_6$ was dried overnight in a vacuum oven at 80–90° C. before each experiment. The solvent was N,N-dimethylformamide (DMF), and it was used as received without further purification. The solvent was transferred to the electrochemical cell via syringe under an argon atmosphere to minimize atmospheric moisture uptake.

Electrochemical measurements were made by first preparing a 0.1 molar solution of TBA $PF_6$ in DMF. This solution was added to the cell, which contained a small magnetic stir bar, as argon gas was flowing through the cell. After the reference and counter electrodes were connected to the instrumentation, the working electrode was polished as described above and was then inserted into the cell. A background scan was conducted before the exemplary compounds were added to the cell. Then, approximately 10 mg of the compound was added to the cell and, after it had dissolved, the measurement was made to record the oxidation potential. The potential was determined at the peak current for the oxidation or reduction reaction on the first scan. In this configuration, the oxidation potential of ferrocene in an identical electrolyte solution appeared at +0.1 volts versus the reference electrode.

Measurement of Oxidative Stability

The oxidative stability of the exemplary substituted arylsulfinates was determined by proton nuclear magnetic resonance spectroscopy. Spectra of solutions of the compounds in acetonitrile-$d_3$ were obtained at regular intervals. The resonances of the alkyl groups in the cations were used as an internal standard to assess the oxidation of the anion.

Preparative Example 1

Preparation of 4-Cyanobenzenesulfonyl Chloride

An intimate mixture 4-carboxybenzenesulfonamide (188 g) and $PCl_5$ (430 g) was made by combining the solids in a resealable plastic bag and manually kneading and shaking the bag. The mixture was transferred to a round bottom flask that was fitted with a magnetic stir bar and a hose adapter that was connected to a source of nitrogen gas. The flask was slowly heated to 60° C. in an oil bath and was held at 60° C. for 5 hours as the mixture was stirred. The hose adapter was then connected to a water aspirator through a trap that was cooled with dry ice, and the temperature of the oil bath was increased to 110° C. while the flask was evacuated and liquid distilled into the trap. When the rate of distillation slowed, the hose adapter was again connected to the nitrogen source and the temperature of the oil bath was raised to 155° C. After an additional 13 hours, the hose adapter was again connected to a water aspirator through a trap and more liquid was distilled. The reaction flask was then allowed to cool to room temperature, during which time the brown product solidified. The crude product was vacuum distilled, using a Kugelrohr distillation (available from Aldrich Chemical Co., Milwaukee, Wis.) at a temperature of 150° C. and a pressure of 0.07 mmHg, into a collection bulb that was cooled in an ice bath. The solid yellow distillate was washed from the collection bulb with $CH_2Cl_2$ and that solution was concentrated to dryness with a rotary evaporator to afford 167.4 g of product.

Preparative Example 2

Preparation of Potassium 4-Ethoxycarbonylbenzenesulfonate

A mixture of sodium 4-carboxybenzenesulfonate (75 g) in deionized water (1200 mL) was heated to 60° C. until the solid was dissolved. This solution was passed through a column of a strongly acidic ion-exchange resin (available under the trade designation AMBERLITE IR-120(PLUS) from Rohm and Haas Co., Philadelphia, Pa.) that had been acidified by washing sequentially with deionized water, concentrated aqueous HCl and deionized water until the pH of the eluate was approximately 5.5. The column was then charged with the solution of sodium 4-carboxybenzenesulfonate and was then washed with deionized water until a total of 2 L of eluate was collected. The deionized water was removed with a rotary evaporator and the resultant intermediate was dried in a vacuum oven overnight at 50° C.

The intermediate was then dissolved in anhydrous ethanol (1 L) in a round bottom flask fitted with a magnetic stir bar, a condenser and a hose adapter that was attached to a source of nitrogen gas. This solution was stirred and heated overnight in an oil bath at 100° C. An additional 500 mL of ethanol was added to the flask and heating and stirring was continued for an additional 4 hours. The solution was allowed to cool to room temperature and was neutralized with alcoholic KOH to the bromothymol blue endpoint. The product precipitated from the solution and was isolated by vacuum filtration, washed with anhydrous ethanol and dried overnight at room temperature to afford 75.1 g of product.

Preparative Example 3

Preparation of 4-Ethoxycarbonylbenzenesulfonyl Chloride

A round bottom flask, fitted with a magnetic stir bar and a hose adapter connected to a source of nitrogen gas, was charged with a solution of potassium 4-ethoxycarbonylbenzenesulfonate (75.1 g) dissolved in a 3:1 (v/v) mixture of acetonitrile (300 mL) and sulfolane (100 mL). As the solution was stirred, $POCl_3$ (55 mL) was added slowly and the stirring mixture was heated at 75° C. under a nitrogen atmosphere for 3 hours. The heterogeneous reaction mixture was allowed to cool to room temperature and was then concentrated using a rotary evaporator. The flask was then cooled in an ice bath and ice was added to the mixture in the flask. The product crystallized as a white solid and was filtered and washed with cold deionized water. The product was dried under vacuum at room temperature and 3 mmHg for 2 hours to afford 76 g of white solid.

Preparative Example 4

Preparation of 1-Chlorosulfonylanthraquinone

Sodium anthraquinone-1-sulfonate (50.0 g) was combined with $POCl_3$ (31 mL) and a 1:2 (v/v) mixture of sulfolane (100 mL) and acetonitrile (200 mL). The mixture was stirred and heated to 110° C. under a nitrogen atmosphere for 44 hours. The mixture was allowed to cool to room temperature and was then further cooled in a refrigerator. The mixture was filtered and the filtrate was poured onto ice in a beaker and this mixture was stirred for 1 hour. The brown precipitate was filtered, washed with deionized water, dried in air and then further dried overnight in a vacuum oven at 45° C. and less than 1 mmHg pressure to give 12.08 g of the product as a brown solid.

Preparative Examples 5–8

Preparation of Substituted Alkali Metal Benzenesulfinates

Substituted alkali metal benzenesulfinates were prepared by hydrolysis of the substituted benzenesulfonyl chlorides that were obtained commercially or were prepared as described in Preparative Examples 1 and 3. Each substituted benzenesulfonyl chloride was stirred for 3 hours at 75° C. in deionized water, at a concentration of 0.2 g of substituted benzenesulfonyl chloride per milliliter of deionized water, with 2.5 equivalents of $Na_2SO_3$ and 2.5 equivalents of $NaHCO_3$ in a round bottom flask. Each reaction mixture was then allowed to cool to room temperature and was then cooled in a refrigerator to 10° C. Each cold solution was acidified with concentrated sulfuric acid until the pH was less than 1.

Each precipitated solid was extracted into ethyl acetate and then the organic phase was evaporated to dryness using a rotary evaporator to afford the substituted benzenesulfinic acid as a colorless solid. Each of the solid substituted benzenesulfinic acids was dissolved in methanol to give approximately 10 weight percent solutions. Deionized water was then added dropwise to each solution until a precipitate just formed. Sufficient methanol was then added to the solution until all of the solid dissolved. Each aqueous methanol solution was neutralized with a 1M aqueous solution of an alkali metal hydroxide (MOH), as indicated in Table 1, to afford the substituted alkali metal substituted benzenesulfinate salts, which were isolated by removal of the solvent with a rotary evaporator.

TABLE 1

Preparative Examples 5–8

| Preparative Example | Benzene-sulfonyl chloride | Wt. Benzene-sulfonyl chloride | MOH | Wt. Benzene-sulfinate |
|---|---|---|---|---|
| 5 | 4-Cyano | 11.68 g | NaOH | 9.30 g |
| 6 | 4-Ethoxycarbonyl | 6.46 g | LiOH | 3.17 g |
| 7 | 4-Chloro | 5.11 g | LiOH | 3.06 g |
| 8 | 4-Trifluoromethyl | 6.20 g | NaOH | 4.15 g |

Preparative Example 9

Preparation of 1-methoxy-4-(2-ethylhexyloxy)benzene

A mixture of 4-methoxyphenol (100.0 g), dry potassium carbonate (166.7 g), acetonitrile (800 mL), and 2-ethylhexyl bromide (173.8 g) was stirred mechanically and heated at reflux for 4 days. The mixture was then allowed to cool to room temperature and was diluted with 1.5 L of deionized water, after which the organic phase was separated. The aqueous phase was extracted with hexane, and the combined organic layers were washed two times with a 1.0 moles/liter aqueous solution of NaOH and were then dried over $MgSO_4$. The solvent was removed under reduced pressure to give an orange oil. The crude product was distilled under reduced pressure to give 152 g of a clear oil (bp 135–138° C. at 0.4 mmHg).

Preparative Example 10

Preparation of 2,5-bis(bromomethyl)-1-methoxy-4-(2-ethylhexyloxy)benzene

A mixture of the product from Preparative Example 9 (50.0 g), paraformaldehyde (30.0 g), acetic acid (100 mL) and HBr (30% in acetic acid, 100 mL) was heated with stirring to 70° C. The reaction spontaneously warmed to 80° C. and the paraformaldehyde dissolved completely to give an orange solution. The mixture was heated and stirred for 4 hours at 70° C., after which time the reaction was cooled to room temperature. The mixture was diluted with methylene chloride (500 mL), the organic layer was separated, washed three times with deionized water, once with saturated $NaHCO_3$, and was then dried over $MgSO_4$. Solvent removal under reduced pressure afforded a pale yellow solid that was recrystallized from hexane to give 71.6 g of a light yellow powder.

Preparative Example 11

Preparation of 2-(2-ethylhexoxy)-5-methoxy-1,4-bis(benzyl)phosponate

A mixture of the product from Preparative Example 10 (28.26 g) and triethyl phosphite (37.4 g) was stirred and heated to reflux for 6 h. After cooling, the product was heated under high vacuum to remove residual triethylphosphite. A thick oil was obtained which slowly crystallized after several days and was used without further purification.

Preparative Example 12

Preparation of bis-[4-(Diphenylamino)stryl]-1-(2-ethylhexyloxy)-4-(methoxy)benzene (KL68 Dye)

To a mixture of the product from Preparative Example 11 (11.60 g), 4-diphenylaminobenzaldehyde (12.34 g), and dry tetrahydrofuran (400 mL), a 1.0M solution of potassium tert-butoxide in tetrahydrofuran (44 mL) was added dropwise as the mixture was stirred. This mixture was stirred for 3 hours at room temperature, then the solvent was removed under vacuum. Deionized water (100 mL) was added to the residue, and the mixture was extracted several times with methylene chloride. The combined organic layers were washed with saturated aqueous NaCl, dried over $MgSO_4$ and then the solvent was removed under vacuum. The crude product was purified by column chromatography on silica gel using 30/70 (v/v) methylene chloride/hexane as the mobile phase. Solvent removal using a rotary evaporator afforded 14.44 g the product as a bright green solid.

Preparative Example 13

Preparation of N,N-Dimethylmorpholinium Hydroxide

To a stirred solution of N-methylmorpholine (10.0 g) in 1,2-dichloroethane (125 mL) at room temperature there was added methyl iodide (14.1 g). The colorless precipitate that formed was filtered and was washed sequentially with 1,2-dichloroethane and petroleum ether. The solid was dried in air at room temperature to afford 21.3 g of product. A sample of this product (1.0 g) was dissolved in deionized water (2 mL) and was passed through a column of strongly basic ion-exchange resin (available under the trade designation DOWEX 1X2-100 from Dow Chemical Co., Midland, Mich.) that had been washed sequentially with 10 g of a 10% aqueous solution of NaOH and 200 mL of deionized water. The sample was washed from the column with 25 mL of deionized water. The eluted solution was concentrated to dryness using a rotary evaporator and was further dried using a vacuum oven at 50° C. overnight to give the product as a colorless solid.

Preparative Example 14

Preparation of 1-Methyl-4-aza-1-azoniabicyclo[2.2.2]octane Hydroxide

To a stirred solution of 1,4-diazabicyclo[2.2.2]octane (10.0 g) in 1,2-dichloroethane (100 mL) at room temperature there was added methyl iodide (12.7 g). The colorless precipitate that formed was filtered and was washed sequentially with 1,2-dichloroethane and petroleum ether. The solid was dried in air at room temperature to afford 21.3 g of product. All of this product was then dissolved in deionized water (200 mL) and was stirred at room temperature while ammonium hexafluorophosphate (13.7 g) was slowly added to the solution. The colorless precipitate that formed was vacuum filtered and was washed with a small amount of deionized water. The solid was allowed to dry in air at room temperature overnight and was further dried using a vacuum oven at 60° C. overnight to afford 7.1 g of product. A sample of this product (1.0 g) was dissolved in deionized water (2 mL) and was passed through a column of strongly basic ion-exchange resin (available under the trade designation DOWEX 1X2-100 from Dow Chemical Co., Midland, Mich.) that had been washed sequentially with 10 g of a 10% aqueous solution of NaOH and 200 mL of deionized water. The sample was washed from the column with 25 mL of deionized water. The eluted solution was concentrated to dryness using a rotary evaporator and was further dried using a vacuum oven at 50° C. overnight to give the product as a colorless solid.

Preparative Example 15

Preparation of 3-Ethyl-2-methylbenzoxazolium Chloride

A solution of 3-ethyl-2-methylbenzoxazolium iodide (1.0 g) in deionized water (20 mL) was passed through a column of ion-exchange resin (available under the trade designation DOWEX 1X2-100 from Dow Chemical Co., Midland, Mich.) that had been washed sequentially with deionized water (200 mL), saturated aqueous NaCl (50 mL), and deionized water (200 mL). The product was washed from the column with approximately 50 mL of deionized water and was concentrated to dryness using a rotary evaporator to afford 0.73 g of product.

Preparative Examples 16–19

Preparation of Substituted Tetrabutylammonium Benzenesulfinates

Tetrabutylammonium benzenesulfinates were prepared from the corresponding alkali metal sulfinates. Each alkali metal sulfinate was dissolved in deionized water to give a 0.1M solution that was acidified with concentrated sulfuric acid to afford the sulfinic acid as a colorless precipitate. Each mixture was extracted with ethyl acetate and then the organic phase was evaporated to dryness using a rotary evaporator. Each resultant solid was dissolved in 50% (v/v) aqueous methanol and this solution was titrated with an aqueous solution of tetrabutylammonium hydroxide. Each mixture was evaporated to dryness using a rotary evaporator to afford the product as a yellow oil. The $^1$H and $^{13}$C NMR spectra of each compound were consistent with the assigned structure. Details of these preparations and oxidation and stability data are given in Table 2.

TABLE 2

Preparative Examples 16–19

| | Preparative Example | | | |
|---|---|---|---|---|
| | 16 | 17 | 18 | 19 |
| Alkali Metal Benzenesulfinate | 4-Chloro | 4-Ethoxy-carbonyl | 4-Trifluoro-methyl | 4-Cyano |
| Wt. Alkali Metal Benzenesulfinate | 0.50 g | 0.58 g | 1.72 g | 2.00 g |
| Wt. Tetrabuylammonium Benzenesulfinate | 0.98 g | 1.27 g | 3.51 g | 4.18 g |
| $E_{ox}$ | 0.09 V | 0.11 V | 0.18 V | 0.15 V |
| $t_{1/2}$(days) | 138 | 174 | 88 | >300 |

Preparative Example 20

Preparation of emim 4-Methylbenzenesulfinate

A mixture of sodium 4-methylbenzenesulfinate (3.1 g) and anhydrous ethanol (80 mL) in a round bottom flask, fitted with a magnetic stir bar, was heated to approximately 75° C. with stirring. The mixture was allowed to cool to approximately 40° C. and then a solution of 1-ethyl-3-methylimidazolium chloride (2.0 g) in anhydrous ethanol (20 mL) was added to the flask. The mixture was stirred for 2 hours after which time it was filtered. The filtrate was concentrated to dryness using a rotary evaporator to give a heterogeneous yellow oil which was taken up in $CHCl_3$. This mixture was filtered and then the filtrate was concentrated to dryness using a rotary evaporator to afford 3.12 g of the product as a yellow oil.

Preparative Example 21

Preparation of Tetraphenylphosphonium 4-Cyanobenzenesulfinate

A solution of sodium 4-cyanobenzenesulfinate (1.0 g) in anhydrous ethanol (100 mL) was prepared in a 250 mL Erlenmeyer flask by heating the solution to boiling on a hot plate with magnetic stirring. To the boiling solution was added a hot solution of tetraphenylphosphonium chloride (1.98 g) in anhydrous ethanol (50 mL) with constant stirring. The stirring solution was allowed to cool for 30 minutes, during which time a colorless precipitate appeared. The flask was then cooled in an ice-bath for an additional 30 minutes with stirring. The mixture was vacuum filtered and the filtrate was dried using a rotary evaporator to yield a deep yellow oil that contained some solid material. This residue was dissolved in chloroform (50 mL) and the mixture was stirred for 20 minutes and was then vacuum filtered. The deep yellow solution was concentrated to dryness using a rotary evaporator to afford a clear yellow oil that was further dried under vacuum for 1 hour at 3 mmHg to yield 2.20 g of the product as a bright yellow wax.

Preparative Example 22

Preparation of Tetrabutylammonium Anthraquinone-1-sulfinate

A solution of 1-chlorosulfonylanthraquinone (12.05 g) was combined with deionized water (200 mL), $Na_2SO_3$ (18.34 g) and $NaHCO_3$ (12.22 g) in a round bottom flask.

The mixture was stirred and heated under a nitrogen atmosphere at 65° C. for 2 hours. The solution was then allowed to cool to room temperature and was then further cooled in a refrigerator. The precipitated solid that formed was isolated by filtration and was allowed to dry in air. The solid was transferred to a flask to which was added 200 mL of a 2:1 (v/v) mixture of methanol and deionized water. The solution was titrated with 40% aqueous tetrabutylammonium hydroxide until a deep red color persisted. The solvent was removed with a rotary evaporator and the deep red oil was dried under high vacuum for 2 days at 45° C. to afford 16.98 g of product.

Preparative Example 23

Preparation of Tetrabutylammonium Naphthalene-1-sulfinate

A round bottom flask was charged with 1-naphthalene-sulfonyl chloride (20.0 g), $Na_2SO_3$ (33.36 g), $NaHCO_3$ (22.24 g) and deionized water (350 mL). The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$ which resulted in the formation of a precipitate. The mixture was extracted three times with 100 mL of ethyl acetate. The organic extracts were combined and the solvent was removed with a rotary evaporator to give a colorless solid that was then dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 36.4 g of a yellow waxy solid.

Preparative Example 24

Preparation of Tetrabutylammonium Naphthalene-2-sulfinate

A round bottom flask was charged with 2-naphthalene-sulfonyl chloride (24.73 g), $Na_2SO_3$ (41.25 g), $NaHCO_3$ (41.25 g) and 350 mL deionized water. The mixture was stirred and heated to 65° C. under a nitrogen atmosphere for 2 hours, after which time the mixture was allowed to cool to room temperature and was then further cooled in a refrigerator. The cold mixture was acidified with concentrated $H_2SO_4$, which resulted in the formation of a precipitate. The mixture was extracted three times with 100 mL of ethyl acetate. The organic extracts were combined and the solvent was removed with a rotary evaporator to give a colorless solid that was then dissolved in 240 mL of 1:1 (v/v) methanol-deionized water in a beaker. The solution was titrated with a solution of 40% aqueous tetrabutylammonium hydroxide until the pH of the solution was 7.2. The solvent was removed with a rotary evaporator and the product was further dried in a vacuum oven at room temperature to afford 46.9 g of a yellow waxy solid.

Preparative Example 25

Preparation of N,N-Dimethylmorpholinium 4-Cyanobenzenesulfinate

Concentrated sulfuric acid was slowly added to a solution of sodium 4-cyanobenzenesulfinate (0.15 g) in deionized water (10 mL). A precipitate formed and sulfuric acid was added dropwise until it appeared that no more precipitate was forming. The mixture was extracted twice with ethyl acetate (20 mL) and the combined organic phases were concentrated to dryness using a rotary evaporator. The resultant solid was dissolved in 50 weight percent aqueous methanol and this solution was titrated with a solution of N,N-dimethylmorpholinium hydroxide (0.85 g) in deionized water (5 mL). The solution was concentrated to dryness using a rotary evaporator and was further dried using a vacuum oven at room temperature overnight. The resultant solid was then dissolved in deionized water and this solution was extracted twice with ethyl acetate (20 mL). The combined organic phases were concentrated to dryness using a rotary evaporator. The resultant solid was further dried using a vacuum oven overnight at room temperature to afford 0.24 g of product as a yellow oil.

Preparative Example 26

Preparation of 1-Methyl-4-aza-1-azoniabicyclo[2.2.2]octane 4-Cyanobenzenesulfinate Concentrated sulfuric acid was slowly added to a solution of sodium 4-cyanobenzenesulfinate (0.25 g) in deionized water (10 mL). A precipitate formed and sulfuric acid was added dropwise until it appeared that no more precipitate was forming. The mixture was extracted twice with ethyl acetate (20 mL) and the combined organic phases were concentrated to dryness using a rotary evaporator. The resultant solid was dissolved in 50 weight percent aqueous methanol and this solution was titrated with a solution of the product of Preparative Example 14 (0.27 g) in deionized water (5 mL) to a pH of approximately 7.2. The solution was concentrated to dryness using a rotary evaporator and was further dried using a vacuum oven at room temperature overnight to afford 0.45 g of product as a yellow waxy solid.

Preparative Example 27

Preparation of N-Hexadecylpyridinium 4-Cyanobenzenesulfinate

A solution of N-hexadecylpyridinium chloride (1.6 g) in ethanol (20 mL) was added to an Erlenmeyer flask containng a magnetically stirred boiling solution of sodium 4-cyanobenzenesulfinate (1.0 g) in anhydrous ethanol (200 mL). The mixture was allowed to cool to room temperature and was then further cooled in an ice bath. The mixture was filtered and the filtrate was concentrated to dryness using a rotary evaporator. The residue was then dissolved in chloroform (100 mL), filtered, and concentrated to dryness using a rotary evaporator to afford 2.4 g of product.

Preparative Example 28

Preparation of 3-Ethyl-2-methylbenzoxazolium 4-Cyanobenzenesulfinate

A solution of 3-ethyl-2-methylbenzoxazolium chloride (0.73 g) in ethanol (20 mL) was added to an Erlenmeyer flask containing a magnetically stirred boiling solution of sodium 4-cyanobenzenesulfinate (0.1 g) in anhydrous ethanol (20 mL). The mixture was allowed to cool to room temperature and was then further cooled in an ice bath. The mixture was filtered and the filtrate was concentrated to dryness using a rotary evaporator. The residue was mixed with deionized water and this mixture was extracted with ethyl acetate (2×20 mL). The combined organic extracts were concentrated to dryness using a rotary evaporator. The resultant solid was then dissolved in methylene chloride, filtered and evaporated to dryness using a rotary evaporator to afford 0.08 g of product.

Examples 1–3

Photocuring of 4-HBA Using Arylsulfinate Salts, Methylene Blue and Diphenyliodonium Hexafluorophosphate A stock solution of 4-HBA and methylene blue was prepared by dissolving methylene blue in 4-HBA to provide a solution that was lightly colored. Sufficient diphenyliodonium hexafluorophosphate was added to form a solution having 1 weight percent of the iodonium salt. Screw-cap vials were charged with approximately 1 g of this solution. An amount of an arylsulfinate salt was added to each vial to give a salt concentration of 1 weight percent. Each solution was purged with nitrogen gas for 45 seconds after which time the vials were sealed. Each solution was irradiated with 100 W quartz-tungsten-halogen (QTH) light source (model I-100, available Cuda Fiberoptics, Jacksonville, Fla.) by holding and slowly agitating each vial approximately 2 cm in front of the light source. The light source shutter was fully open. Cure time was considered to be the time that it took for the solution to no longer flow in the vial as the vial was agitated. The results are given in the Table 3.

TABLE 3

Curing of Examples 1–3

| Example | Arylsulfinate Salt | Cure Time (sec) |
|---|---|---|
| 1 | Tetrabutylammonium Anthraquinone-1-sulfinate | 6 |
| 2 | Tetrabutylammonium Naphthalene-1-sulfinate | <2 |
| 3 | Tetrabutylammonium Naphthalene-2-sulfinate | <2 |

Examples 4–15

Photocuring of HEA using Tetrabutylammonium 4-Cyanobenzenesulfinate with Diphenyliodonium Hexafluorophosphate To a stock solution of HEA and 1 weight percent tetrabutylammonimum 4-cyanobenzenesulfinate there was added sufficient diphenyliodonium hexafluorohosphate to give a solution having 1 weight percent of the iodonium salt. Screw-cap vials were charged with approximately 1 g of this solution. An amount of a dye was added to each vial to give a dye concentration sufficient to provide a lightly colored solution, typically between 50 and 1000 ppm, depending on the dye. Each solution was purged with nitrogen gas for 30 seconds after which time the vials were sealed. Each solution was irradiated as described in Examples 1–3. The results are given in Table 4.

TABLE 4

Curing of Examples 4–15

| Example | Dye | Cure time (sec) | Uncured color | Cured Color |
|---|---|---|---|---|
| 4 | Methylene Green | 2 | Green | Colorless |
| 5 | Fluorescein | 4 | Green-yellow | Green |
| 6 | Methylene blue | 4 | Blue | Pale yellow |
| 7 | Rose bengal | 4 | Red | Pale red |
| 8 | Acridine orange | 6 | Orange | Orange |
| 9 | Methylene violet | 7 | Violet | Red-violet |
| 10 | Rhodamine 6G | 7 | Pink | Pink |
| 11 | Cyanine 1 | 9 | Blue-green | Blue-violet |
| 12 | Basic Blue 3 | 10 | Blue | Blue |
| 13 | Coumarin | 153 | Yellow | Yellow |
| 14 | Nile Blue Chloride | 10 | Blue | Blue |
| 15 | Methyl Orange | 70 | Orange | Orange |

Examples 16–20

Photocuring of 4-HBA Using 4-Cyanobenzenesulfinates with Diphenyliodonium Hexafluorophosphate and Methylene Blue To approximately 1 g each of solutions 4-HBA and 1 weight percent of the 4-cyanobenzenesulfinate salts of Preparative Examples 21, 25, 26, 27, and 28 in individual screw cap vials there was added sufficient diphenyliodonium hexafluorophosphate to give a solution comprising 1 weight percent of the iodonium salt. An amount of methylene blue was added to each vial to give a dye concentration sufficient to provide lightly colored solutions. Each solution was purged with nitrogen gas for 1 minute after which time the vials were sealed. Each solution was irradiated as described in Examples 1–3. The results are given in Table 5.

TABLE 5

Curing of Examples 16–20

| Example | 4-Cyanobenzenesulfinate salt | Cure time (sec) |
|---|---|---|
| 16 | Tetraphenylphosphonium | <4 |
| 17 | N,N-Dimethylmorpholinium | <4 |
| 18 | 1-Methyl-4-aza-1-azoniabicylco[2.2.2]octane | <4 |
| 19 | N-Hexadecylpyridinium | <4 |
| 20 | 3-Ethyl-2-methylbenzoxazolium | <3 |

Examples 21–24

Photocuring of 4-HBA Using Substituted Benzenesulfinates And Basic Blue 3

Mixtures 4-HBA (0.5 g) with 1 weight percent diphenyliodonium hexafluorophosphate, 20 ppm of Basic Blue 3, and 27 micromoles per gram of the substituted tetrabutylammonium benzenesulfinates of Preparative Examples 16–19 were prepared. Each sample was evaluated for rate and extent of cure by photo differential scanning calorimetry (photo-DSC) using a model DSC2920 calorimeter (available from TA Instruments, New Castle, Del.) with actinic radiation lower in energy than 300 nm at an irradiance of 20 mW/cm$^2$. The results are given in Table 6.

TABLE 6

Curing of Examples 21–24

| Example | Substituted tetrabutylammonium benzenesulfinate | Initial Slope (W/g-min) | Time to peak maximum (min) | Total evolved heat (J/g) |
|---|---|---|---|---|
| 21 | 4-Chloro | 94.1 | 0.25 | 438.7 |
| 22 | 4-Ethoxycarbonyl | 115.1 | 0.24 | 509.2 |
| 23 | 4-Trifluoromethyl | 86.9 | 0.27 | 501.1 |
| 24 | 4-Cyano | 121.4 | 0.24 | 509.8 |

Examples 25–28

Photocuring of 4-HBA Using Substituted Arylsulfinates And KL68 Dye

Mixtures of 0.5 g 4-HBA with 1 weight percent diphenyliodonium hexafluorophosphate, 71 ppm of KL68 Dye and 1 weight percent of each of the substituted tetrabutylammonium benzenesulfinates of Preparative Examples 16–19 were prepared. Each sample was evaluated for rate and extent of cure by photo differential scanning calorimetry as described in Examples 21–24. The results are given in the Table 7.

TABLE 7

Curing of Examples 25–28

| Example | Substituted tetrabutylammonium benzenesulfinate | Initial Slope (W/g-min) | Time to peak maximum (min) | Total evolved heat (J/g) |
|---|---|---|---|---|
| 25 | 4-Chloro | 94.4 | 0.26 | 487.0 |
| 26 | 4-Ethoxycarbonyl | 125.7 | 0.24 | 522.3 |
| 27 | 4-Trifluoromethyl | 116.6 | 0.24 | 516.1 |
| 28 | 4-Cyano | 152.3 | 0.21 | 518.1 |

Examples 29–32

Photocuring of 4-HBA Using A Substituted Benzenesulfinate And Near-IR Dyes

Mixtures of 4-HBA (5.0 g) with 1 weight percent diphenyliodonium hexafluorophosphate, 1 weight percent of the product of Preparative Example 17 and approximately 0.1 weight percent of either near-IR dye IR140 or near-IR dye IR780 iodide were prepared in screw-cap vials. The solutions were purged with nitrogen gas and then each sample was irradiated with a QTH light source as described in Examples 1–3. Separately, samples of the mixtures were purged with nitrogen gas and were then irradiated with actinic radiation from a QTH light source that was filtered with a RG715 long pass filter (available from Esco Products, Oak Ridge, N.J.). The results are given in Table 8.

TABLE 8

Examples 29–32

| Example | Near-IR Dye | RG715 filter | Cure time (sec) |
|---|---|---|---|
| 29 | IR140 | No | 15 |
| 30 | IR140 | Yes | >60 |
| 31 | IR780 iodide | No | 8 |
| 32 | IR780 iodide | Yes | 30 |

Examples 33–35

Thermal Polymerization of Acrylate Monomer

Compositions of SR238, SR339, or SR399, each with 1 weight percent diphenyliodonium hexafluorophosphate and 1 weight percent of the product of Preparative Example 19 were prepared in screw-cap vials. The vials were sealed and were allowed to stand in the dark at room temperature. The mixtures were periodically examined to assess the viscosity by manually tipping the vials to observe the flow of the liquids. Polymerization time was considered to be the time until the mixture no longer flowed in the vial. The results are given in Table 9.

TABLE 9

Examples 33–35

| Example | Monomer | Polymerization time |
|---|---|---|
| 33 | SR238 | <5 min |
| 34 | SR339 | <5 min |
| 35 | SR399 | <5 min |

Example 36

Thermal Polymerization of Trimethylolpropane Triacrylate

A mixture of SR351, 1 weight percent diphenyliodonium hexafluorophosphate, and 1 weight percent of the product of Preparative Example 19 was prepared in a screw-cap vial. The vial was sealed and was allowed to stand in the dark at room temperature. The mixture was periodically examined to assess the viscosity by manually tipping the vials and observing the flow of the mixture. The polymerization time, considered to be the time until the mixture no longer flowed in the vial, was found to be less then 3 minutes.

Example 37

Thermal Polymerization of Trimethylolpropane Triacrylate

A mixture of SR351, 0.5 weight percent diphenyliodonium hexafluorophosphate, and 0.5 weight percent of the product of Preparative Example 18 was prepared in a screw-cap vial. The vial was sealed and was allowed to stand in the dark at room temperature. The mixture was periodically examined to assess the viscosity by manually tipping the vials and observing the flow of the mixture. The polymerization time, considered to be the time until the mixture no longer flowed in the vial, was found to be less then 5 minutes.

We claim:

1. A composition comprising:
    an electron donor comprising an arylsulfinate salt having a anion of Formula I

and a cation having at least one carbon atom and either a positively charged nitrogen atom or a positively charged phosphorus atom, said electron donor having an oxidation potential in N,N-dimethylformamide of 0.0 to +0.4 volts versus a silver/silver nitrate reference electrode, wherein
    $Ar^1$ is a substituted phenyl, an unsubstituted or substituted $C_{7-30}$ aryl, or an unsubstituted or substituted $C_{3-30}$ heteroaryl, said substituted $Ar^1$ having a substituent that is an electron withdrawing group or an electron withdrawing group in combination with an electron donating group;
    the cation is selected from
        1) a phosphorous-containing cation of Formula III

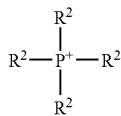

where each $R^2$ is independently an unsubstituted alkyl, an alkyl substituted with a hydroxy, an unsubstituted aryl, or an aryl substituted wit an alkyl, hydroxy, or combinations thereof; or
        2) a nitrogen-containing cation having a ring structure comprising a 4 to 12 member heterocyclic group having a positively charged nitrogen atom, said heterocyclic being saturated or unsaturated and having up to 3 heteroatoms selected from oxygen, sulfur, nitrogen, or combinations thereof, wherein said ring structure is unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof; and
    an electron acceptor having a reduction potential in N,N-dimethylformamide of +0.4 to −1.0 volts versus a silver/silver nitrate reference electrode.

2. The composition of claim 1, wherein the $Ar^1$ group of the arylsulfinate salt is anthryl, naphthyl, acenaphthyl, phenanthryl, phenanthrenyl, perylenyl, anthracenyl, anthraquinonyl, anthronyl, biphenyl, terphenyl, 9,10-dihydroanthracenyl, or fluorenyl, said $Ar^1$ group being unsubstituted or substituted with an electron withdrawing group or an electron withdrawing group in combination with an electron donating group.

3. The composition of claim 1, wherein the $Ar^1$ group of the arylsulfinate salt is quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, or indazolyl, said $Ar^1$ group being unsubstituted or substituted with an electron withdrawing group or an electron withdrawing group in combination with an electron donating group.

4. The composition of claim 1, wherein the $Ar^1$ group of the arylsulfinate salt is a substituted phenyl, an unsubstituted or substituted naphthyl, or an unsubstituted or substituted anthraquinonyl, said substituted $Ar^1$ having a substituent that is an electron withdrawing group or an electron withdrawing group in combination with an electron donating group.

5. The composition of claim 1, wherein the $Ar^1$ group is phenyl substituted with an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, aminocarbonyl, or combinations thereof.

6. The composition of claim 1, wherein the anion of the arylsulfinate salt is 4-chlorobenzenesulfinate, 4-cyanobenzenesulfinate, 4-ethoxycarbonylbenzenesulfinate, 4-trifluoromethylbenzenesulfinate, 3-trifluoromethylbenzenesulfinate, 1-anthraquinone sulfinate, 1-naphthalenesulfinate, or 2-naphthalenesulfinate.

7. The composition of claim 1, wherein the cation of the arylsulfinate salt is the ring structure comprising a 5 member heterocyclic group, a 5 member heterocyclic group fused to an aromatic ring having 0 to 3 heteroatoms, a 6 member heterocyclic group, or a 6 member heterocyclic group fused to an aromatic ring having 0 to 3 heteroatoms, wherein said ring structure is unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

8. The composition of claim 1, wherein said heterocyclic group is bicyclic.

9. The composition of claim 1, wherein said heterocyclic group is fused to a cyclic or bicyclic group that is saturated or unsaturated and that has 0 to 3 heteroatoms.

10. The composition of claim 1, wherein said heterocyclic group is fused to an aromatic ring having 0 to 3 heteroatoms.

11. The composition of claim 1, wherein the cation of the arylsulfinate salt is of Formula III where each $R^2$ is independently an unsubstituted aryl or an aryl substituted with an alkyl, hydroxy, or combinations thereof.

12. The composition of claim 1, wherein the electron acceptor is an iodonium salt, a hexaarylbisimidizole, a persulfate, a peroxide, or a metal ion in an oxidized state.

13. The composition of claim 1, further comprising a sensitizing compound capable of absorbing a wavelength of actinic radiation in the range of 250 to 1000 nanometer.

14. The composition of claim 13, wherein the electron acceptor is a diaryliodonium salt, a hexaarylbisimidizole, or combinations thereof.

15. The composition of claim 13, wherein the electron acceptor has an electron potential in the range of 0.0 to −1.0 volts versus a silver/silver nitrate reference electrode.

16. The composition of claim 1, further comprising an ethylenically unsaturated monomer.

17. The composition of claim 16, wherein the ethylenically unsaturated monomer comprises a monoacrylate, monomethacrylate, diacrylate, dimethacrylate, polyacrylate, polymethacrylate, or combinations thereof, wherein said monomer is unsubstituted or substituted with a hydroxy.

18. The composition of claim 13, wherein the composition further comprises a hydroxy-containing material selected from an alcohol, a hydroxy-containing monomer, or combinations thereof.

19. The composition of claim 1, wherein the cation comprises tetraphenylphosphonium that is unsubstituted or substituted.

20. The composition of claim 1, wherein the cation comprises an imidazolium ion or oxazolium ion that is unsubstituted or substituted.

21. The composition of claim 1, wherein the cation comprises benzoxazolium ion or benzothiazolium ion that is unsubstituted or substituted.

22. The composition of claim 1, wherein the cation comprises a pyridinium ion or morpholinium ion that is unsubstituted or substituted.

23. The composition of claim 1, wherein the cation comprises N-alkylated 1,4-diazabicyclo[2.2.2]octane, N-protonated 1,4-diazabicyclo[2.2.2]octane, N-alkylated 1-azabicyclic[2.2.2]octane, or N-protonated 1,4-diazabicyclo[2.2.2]octane that is unsubstituted or substituted.

* * * * *

UNITED STATES PATENT AND TRADEMARK OFFICE
CERTIFICATE OF CORRECTION

PATENT NO. : 7,030,169 B2  
APPLICATION NO. : 10/672762  
DATED : April 18, 2006  
INVENTOR(S) : Kalgutkar, Rajdeep S.

Page 1 of 1

It is certified that error appears in the above-identified patent and that said Letters Patent is hereby corrected as shown below:

Column 1  
Line 1, after "provided" delete "that".

Column 23  
Line 59, delete "2.5-bis" and insert -- 2,5-bis --, therefor.

Column 26  
Line 13, delete "Tetrabuylammonium" and insert -- Tetrabutylammonium --, therefor.

Column 29  
Line 59, delete "hexafluorohosphate" and insert -- hexafluorophosphate --, therefor.

Column 33  
Line 33, in Claim 1, delete "wit" and insert -- with --, therefor.

Column 34  
Line 9, in Claim 5, delete "pertluoroalkyl," and insert -- perfluoroalkyl, --, therefor.

Signed and Sealed this

Eighteenth Day of July, 2006

JON W. DUDAS  
*Director of the United States Patent and Trademark Office*